US006956027B2

(12) United States Patent
Kinstler

(10) Patent No.: US 6,956,027 B2
(45) Date of Patent: *Oct. 18, 2005

(54) N-TERMINALLY CHEMICALLY MODIFIED PROTEIN COMPOSITIONS AND METHODS

(75) Inventor: Olaf B. Kinstler, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 10/264,846

(22) Filed: Oct. 4, 2002

(65) Prior Publication Data

US 2003/0096400 A1 May 22, 2003

Related U.S. Application Data

(63) Continuation of application No. 10/131,956, filed on Apr. 25, 2002, and a continuation of application No. 09/817,725, filed on Mar. 26, 2001, which is a continuation of application No. 09/408,113, filed on Sep. 29, 1999, now abandoned, which is a division of application No. 08/879,760, filed on Jun. 20, 1997, now Pat. No. 5,958,265, which is a continuation of application No. 08/321,510, filed on Oct. 12, 1994, now Pat. No. 5,824,784.

(51) Int. Cl.[7] .......................... A61K 38/22; A61K 38/16
(52) U.S. Cl. ............................ 514/12; 514/12; 514/21; 424/85.4; 424/85.5; 424/85.7; 424/85.1; 530/406
(58) Field of Search .................... 514/12, 21; 424/85.4, 424/85.1, 85.5, 85.7; 530/406, 351, 402

(56) References Cited

U.S. PATENT DOCUMENTS

| | | | |
|---|---|---|---|
| 1,609,536 A | 12/1926 | Harris |
| 4,002,531 A | 1/1977 | Royer |
| 4,179,337 A | 12/1979 | Davis et al. |
| 4,609,546 A | 9/1986 | Hiratani |
| 4,695,623 A | 9/1987 | Stabinsky |
| 4,766,106 A | 8/1988 | Katre et al. |
| 4,791,192 A | 12/1988 | Nakagawa et al. |
| 4,810,643 A | 3/1989 | Souza |
| 4,833,127 A | 5/1989 | Ono et al. |
| 4,847,325 A | 7/1989 | Shadle et al. |
| 4,894,226 A | 1/1990 | Aldwin et al. |
| 4,897,471 A | 1/1990 | Stabinsky |
| 4,904,584 A | 2/1990 | Shaw |
| 5,166,322 A | 11/1992 | Shaw et al. |
| 5,194,592 A | 3/1993 | Yoshida |
| 5,214,132 A | 5/1993 | Kuga et al. |
| 5,218,092 A | 6/1993 | Sasaki et al. |
| 5,252,714 A | 10/1993 | Harris et al. |
| 5,281,698 A | 1/1994 | Nitecki |
| 5,349,052 A | 9/1994 | Delgado et al. |
| 5,372,808 A | 12/1994 | Blatt et al. |
| 5,382,657 A | 1/1995 | Karasiewicz et al. |
| 5,532,341 A | 7/1996 | Welte et al. |
| 5,581,476 A | 12/1996 | Osslund |
| 5,672,662 A | 9/1997 | Harris et al. |
| 5,824,778 A | 10/1998 | Ishikawa et al. |
| 5,824,784 A | 10/1998 | Kinstler et al. |
| 5,985,265 A | * 11/1999 | Kinstler et al. ............ 424/85.4 |
| 6,027,720 A | 2/2000 | Kuga et al. |
| 6,166,183 A | 12/2000 | Ishikawa et al. |

FOREIGN PATENT DOCUMENTS

| | | |
|---|---|---|
| AU | A-76380/91 | 11/1991 |
| AU | A-10948/92 | 8/1992 |
| EA | 401 384 | 12/1990 |
| EP | 154 316 | 9/1985 |
| EP | 098 110 | 9/1986 |
| EP | 210 761 | 2/1987 |
| EP | 215 126 | 3/1987 |
| EP | 236 987 | 9/1987 |
| EP | 243 153 | 10/1987 |
| EP | 247 860 | 12/1987 |
| EP | 256 843 | 2/1988 |
| EP | 272 703 | 6/1988 |
| EP | 335 423 | 10/1989 |
| EP | 0 340 741 | 11/1989 |
| EP | 370 205 | 5/1990 |
| EP | 442 724 | 8/1991 |
| EP | 456 200 A1 | 11/1991 |
| EP | 459 630 | 12/1991 |
| EP | 473 268 | 3/1992 |
| EP | 473 769 | 3/1992 |
| EP | 490 584 | 6/1992 |
| EP | 539 167 | 4/1993 |
| EP | 721 958 | 7/1996 |
| GB | 2 193 631 | 2/1988 |
| JP | 57-192435 | 11/1982 |
| JP | 61-42558 | 9/1986 |
| JP | 62-115280 | 5/1987 |
| JP | 62-129298 | 6/1987 |
| JP | 62-236488 | 10/1987 |
| JP | 62-236497 | 10/1987 |
| JP | 62-289522 | 12/1987 |
| JP | 62-503171 | 12/1987 |
| JP | 63-10800 | 1/1988 |

(Continued)

OTHER PUBLICATIONS

Abuchowski, et al., in *Enzymes as Drugs*, J.S. Holcerberg and J. Roberts (Eds.), pp. 367–383 (1981).

Asano, et al., "A Colorimetric Microassay for the Biological Activity of Human Granulocyte Colony–Stimulating Factor Using Murine Myeoblastic Leukemia, NSF–60 Cells," *Japan Pharmacol. Ther.*, 19:2767–2773 (1991).

(Continued)

*Primary Examiner*—Christopher R. Tate
*Assistant Examiner*—B. Dell Chism
(74) *Attorney, Agent, or Firm*—Marshall, Gerstein & Borun LLP

(57) ABSTRACT

Provided herein are methods and compositions relating to the attachment of water soluble polymers to proteins. Provided are novel methods for N-terminally modifying proteins or analogs thereof, and resultant compositions, including novel chemically modified G-CSF compositions and related methods of preparation.

28 Claims, 15 Drawing Sheets

FOREIGN PATENT DOCUMENTS

| | | |
|---|---|---|
| JP | 63-60938 | 3/1988 |
| JP | 63-500636 | 3/1988 |
| JP | 63-126900 | 5/1988 |
| JP | 1-26677 | 5/1989 |
| WO | WO-87/01132 | 2/1987 |
| WO | WO-89/10932 | 12/1989 |
| WO | WO-89/05824 | 2/1990 |
| WO | WO-90/04606 | 5/1990 |
| WO | WO-90/09798 | 9/1990 |
| WO | WO-90/12874 | 11/1990 |
| WO | WO-91/05798 | 5/1991 |
| WO | WO-92/06707 | 4/1992 |
| WO | WO-94/00913 | 12/1993 |
| WO | WO-96/11953 | 4/1996 |

OTHER PUBLICATIONS

Balmer, DICP, *The Annals of Pharmacotherapy*, 24:761–767 (1990).

Bensinger, et al., "Autologous Transplantation with Peripheral Blood Mononuclear Cells Collected After Administration of Recombinant Granulocyte Simulating Factor," *Blood* 81(11):3158–3163 (1993).

Bodine, "Mobilization of Peripheral Blood 'Stem' Cells: Where there is smoke, is there fire?" *Experimental Hematology* 23:293–295 (1995).

Boehringer Mannheim, *Biochemica Katalog*, pp. 362 (1994).

Brugger, et al., "Mobilization of Peripheral Blood Progenitor Cells by Sequential Administration of Interleukin–3 and Granulocyte–Macrophage Colony–Stimulating Factor Following Polychemotherapy with Etopside, Ifosamide, and Cisplatin," *Blood* 79:1193–1200 (1992).

Chamow, et al., "Modification of CD4 immunoadhesion with monomethoxypoly(ethylene glycol) aldehyde via reductive alkylation," *Bioconjugate Chem.*, 5:133–140 (1994).

*CRC Standard Mathematical Tables*, 26th Ed. (Beyer, W.H. Ed.) CRC Press, Inc., Boca Raton, FL 1981, p. 125.

Delgado, et al. "The Uses and Properties of PEG–Linked Proteins," *Critical Reviews in Therapeutic Drug Carrier Systems* 9:249–304 (1992).

Delgado, et al., "Coupling of PEG to Protein by Activation with Treysi Chloride, Applications in Immunoaffinity Cell Preparation," in Fisher et al., Eds., Separations Using Aqueous Phase Systems, Applications in Cell Biology and Biotechnology, Plenum Press, New York, NY, pp. 211–213 (1989).

*Filgrastim Clinical Practice*, Morstyn G and T.M. Dexter, eds., Marcel Dekker, Inc., New York NY 1993, p. 351.

Francis, "Protein Modification and Fusion Proteins," *Focus on Growth Factors*, 3:4–10 (May 1992).

Francis, et al., in *Stability of Protein Pharmaceuticals: In Vivo Pathways of Degradation and Strategies for Protein Stabilization*, Ahem, T. and Manning, M.C. (Ed.), Plenum Pres, New York, NY (1991).

Gaertner, et al., "Site specific attachment of functionalized poly(ethylene glycol) to the amino terminus of proteins," *Bioconjugate Chem.*, 7(1):38–44 (1996).

Goodson, et al., "Site–directed Pegylation of recombinant Interleukin–2 at its Glycosylation Site," *Bio/Technology*, 8:343–346 (1990).

Habeeb, "Determination of Free Amino Groups in Proteins by Trinitrobenzenesulfonic Acid," *Anal. Biochem.*, 14:328–336 (1966).

Hershfield, et al., "Treatment of Adenosine Deaminase Deficiency with Polyethylene Glycol–Modified Adenosine Deaminase," *N.E. Journ. of Medicine, 316:* 589–596 (1987).

Hill, et al., "The structure of granulocyte–colony–stimulating factor and its relationship to other growth factors," *Proc. Natl. Acad. Sci., USA* 90 (11):5167–5171 (Jun. 1993).

Inada, et al., "Polyethylene Glycol (PEG)–Protein Conjugates: Application to Biomedical and Biotechnological Processes," *J. Bioact. and Compatible Polymers, 5:*343–364 (1990).

Ishikawa, et al., "The Substitution of Cysteine 17 of Recombinant Human G–CSF with Alanine Greatly Enhanced its Stability," *Cell Structure and Function, 17(1)*:61–65 (Feb. 1992).

Katre, "The Conjugation of Proteins with Polyethylene Glycol and Other Polymers," *Advanced Drug Delivery 10:*91–114 (1993).

Katre, et al., "Chemical Modification of Recombinant Interleukin 2 by Polyethylene Glycol Increases it Potency in the Murine Meth A Sarcoma Model," *Proc. Nat'l Acad. Sci., USA, 85:*1487–1491 (1987).

Klein, et al., "Isolation and structural characterization of Three Isoforms of Recombinant Consensus Alpha Interferon," *Arc Biochem. Biophys., 276:*531–537 (1990).

Klein, et al., "Structural Characterization of Recombinant Consensus Interferon–Alpha," *J. Chromatog. 454:*205–215 (1988).

Kodera, et al., "Frontier of Chemical Modification of Proteins: Application of Polyethylene glycol–modified Enzymes in Biotechnical Processes," *Seikagaku* 60(9):1015–1018 (1988). No English Translation.

Koerholz, et al., "Chemical and Immunological Characteristics of Four Different L–Asparaginase Preparations," *Eur. J. Haematol., 42(5)*:417–424 (1982).

Kuga, et al., "Mutagenesis of Human Granulocyte Colony Stimulating Factor," *Biochem. Biophys. Res. Commun., 159(1)*:103–111 (1989).

Laemmli, "Cleavage of Structural Proteins During the Assembly of the Head of Bacteriophage T4," *Nature* 227:680–685 (1970).

Lu, et al., "Disulfide and Secondary Structures and Recombinant Human Granulocyte Colony Stimulating Factor," *Arch. Biochem. Biophys., 268:*81–92 (1989).

McGoff, et al., "Analysis of Polyethylene Glycol Modified Superoxide Dismutase by Chromatographic, Electrophoretic, Light Scattering Chemical and Enzymatic Methods," *Chem. Pharm. Bull., 36(8)*:3079–3091 (1988).

Metcalf, "The Molecular Biology and Functions of the Granulocyte–Macrophage Colony–Stimulating Factors", *Blood, 67:*257–267 (1986).

Morstyn, "Effects of Granulocyte Colony Stimulating Factor of Neutropenia Induced by Cytotoxic Chemotherapy," *The Lancet,* 667–674 (1998).

Neben, et al., "Mobilization of Hematopoietic Stem and Progenitor Cell Subpopulations from the Marrow to the Blood of Mice Following Cyclophosphamide and/or Granulocyte Colony–Stimulating factor," *Blood, 81(7):*1960–1967 (1993).

Niven, et al., "Pulmonary Absorption of Polyethylene Glycolated Recombinant Human Granulocyte–Colony Stimulating Factor (PEG rhG–CSF)," *J. Controlled Release, 32:*177–189 (1994).

Orlic, et al., "Bone Marrow Cells Regenerate Infarcted Myocardium," *Nature, 410:*701–705 (2001).

Orlic, et al., "Mobilized Bone Marrow Cells Repair the Infarcted heart, Improving Function and Survival," *Proc. Natl. Acad. Sci. USA 18:*10344–10349 (2001).

Ralph, et al., "Inducible Production of Human Macrophage Growth Factor, CSF–1," *Blood 66:*633–639 (1988).

*Remington's Pharmaceutical Sciences,* 18th Edition, Mack Publishing Co., Easton, PA 18042, pp. 1435–1712 (1990).

Roberts, et al., "Granulocyte Colony–Stimulating Factor Induces Selective Elevations of Progenitor Cells in the Peripheral Blood of Mice," *Expt'l. Hematology 22:*1156–1163 (1994).

Rose, et al., "Preparation of Well–Defined Protein Conjugates Using Enzyme–Assisted Reverse Proteolysis," *Bioconjugate Chemistry, 2(3):*154–159 (1991).

Sada, et al., "Resistance to Proteolysis of Antibody Ligands Modified With Polyethylene Glycol," *J. Fermentation and Bioengineering 71(2):*137–139 (1991).

Satake–Ishikawa, et al., "Chemical Modification of Recombinant Human Granulocyte Colony–Stimulating Factor by Polyethylene Glycol Increases its Biological Activity In Vivo," *Cell Structure and Function 17:*157–160 (1992).

Schaper, "Therapeutic Arteriogenesis Has Arrived," *Circulation, 104:* 1994–1995 (2001).

Seiler, et al., "Promotion of Collateral Growth by Granulocyte–Macrophage Colony–Stimulating Factor in Patients with Coronary Artery Disease, A Randomized, Double–Blind, Placebo–Controlled Study," *Circulation 104:*2012–2017 (2001).

Stocks, et al., "A Fluorometric Assay of the Degree of Modification of Protein Primary Amines with Polyethylene Glycol," *Anal. Biochem. 154:*232–234 (1986).

Stryer, in *Biochemistry,* 2nd Edition, Table 4–1, pp. 80 (1981).

Sussman, "Hearts and Bones," *Nature, 410:*640–641 (2001).

Welte, et al., "Purification and Biochemical Characterization of Human Pluripotent Hematopoietic Colony–Stimulating Factor," *Proc. Nat'l. Acad. Sci (USA), 82:* 1526–1530 (1985).

Wetzel, et al., "A General Method for Highly Selective Cross–Linking of Unprotected Polypeptides Via pH–Controlled Modification of N–Terminal Alpha–Amino Groups," *Bioconjugates Chem., 1(2):*114–122 (1990).

Yamasaki, et al., "Modification of Recombinant Human Granulocyte Colony–Stimulating Factor (rhG–CSF) and Its Derivative ND 28 with Polyethylene Glycol," *Biochem., 115:*814–819 (1994).

Yan, et al., "Mobilization of Long–Term Hematopoietic Reconstituting Cells in Mice by the Combination of Stem Cell Factor Plus Granulocyte Colony–Stimulating Factor," *Blood, 84(3):*795–799 (1994).

* cited by examiner

| Lane No. | Sample | ug loaded |
|---|---|---|
| 1 | MW Protein Standards | - |
| 2 | rHuG-CSF Std | 3.0 |
| 3 | SCM-PEG-GCSF Reaction Mix | 10.0 |
| 4 | Species 1 (N-Term) | 10.0 |
| 5 | Species 2 (Lys-35) | 10.0 |
| 6 | Species 3 (Lys-41) | 10.0 |

SEC-HPLC Profiles of
(A) rHuG-CSF standard
(B) SCM-PEG-GCSF Reaction Mixture
(C) Species 1 (N-Term Derivative)
(D) Species 2 (Lys-35 Derivative)
(E) Species 3 (Lys-41 Derivative)

* contains de-Pegylated rHuG-CSF, generated during storage.

N-TERMINALLY CHEMICALLY MODIFIED PROTEIN COMPOSITIONS AND METHODS

FIELD OF THE INVENTION

The present invention broadly relates to the field of protein modification, and, more specifically, the attachment of water soluble polymers to proteins or analogs thereof (the term "protein" as used herein is synonymous with "polypeptide" or "peptide" unless otherwise indicated). The present invention also relates to novel methods for N-terminally modifying proteins or analogs thereof, and resultant compositions. In another aspect, the present invention relates to novel N-terminally chemically modified G-CSF compositions and related methods of preparation. The present invention also relates to chemically modified consensus interferon.

BACKGROUND

Proteins for therapeutic use are currently available in suitable forms in adequate quantities largely as a result of the advances in recombinant DNA technologies. The availability of recombinant proteins has engendered advances in protein formulation and chemical modification. One goal of such modification is protein protection. Chemical attachment may effectively block a proteolytic enzyme from physical contact with the protein backbone itself, and thus prevent degradation. Additional advantages include, under certain circumstances, increasing the stability and circulation time of the therapeutic protein and decreasing immunogenicity. A review article describing protein modification and fusion proteins is Francis, *Focus on Growth Factors* 3: 4–10 (May 1992) (published by Mediscript, Mountview Court, Friern Barnet Lane, London N20, OLD, UK).

Polyethylene glycol ("PEG") is one such chemical moiety which has been used in the preparation of therapeutic protein products (the verb "pegylate" meaning to attach at least one PEG molecule). For example Adagen, a pegylated formulation of adenosine deaminase is approved for treating severe combined immunodeficiency disease; pegylated superoxide dismutase has been in clinical trials for treating head injury; pegylated alpha interferon has been tested in phase I clinical trials for treating hepatitis; pegylated glucocerebrosidase and pegylated hemoglobin are reported to have been in preclinical testing. The attachment of polyethylene glycol has been shown to protect against proteolysis, Sada, et al., J. Fermentation Bioengineering 71: 137–139 (1991), and methods for attachment of certain polyethylene glycol moieties are available. See U.S. Pat. No. 4,179,337, Davis et al., "Non-Immunogenic Polypeptides," issued Dec. 18, 1979; and U.S. Pat. No. 4,002,531, Royer, "Modifying enzymes with Polyethylene Glycol and Product Produced Thereby," issued Jan. 11, 1977. For a review, see Abuchowski et al., in Enzymes as Drugs. (J. S. Holcerberg and J. Roberts, eds. pp. 367–383 (1981)).

Other water soluble polymers have been used, such as copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers).

For polyethylene glycol, a variety of means have been used to attach the polyethylene glycol molecules to the protein. Generally, polyethylene glycol molecules are connected to the protein via a reactive group found on the protein. Amino groups, such as those on lysine residues or at the N-terminus, are convenient for such attachment. For example, Royer (U.S. Pat. No. 4,002,531, above) states that reductive alkylation was used for attachment of polyethylene glycol molecules to an enzyme. EP 0 539 167, published Apr. 28, 1993, Wright, "Peg Imidates and Protein Derivates Thereof" states that peptides and organic compounds with free amino group(s) are modified with an immediate derivative of PEG or related water-soluble organic polymers. U.S. Pat. No. 4,904,584, Shaw, issued Feb. 27, 1990, relates to the modification of the number of lysine residues in proteins for the attachment of polyethylene glycol molecules via reactive amine groups.

One specific therapeutic protein which has been chemically modified is granulocyte colony stimulating factor, "G-CSF." G-CSF induces the rapid proliferation and release of neutrophilic granulocytes to the blood stream, and thereby provides therapeutic effect in fighting infection.

European patent publication EP 0 401 384, published Dec. 12, 1990, entitled, "Chemically Modified Granulocyte Colony Stimulating Factor," describes materials and methods for preparing G-CSF to which polyethylene glycol molecules are attached.

Modified G-CSF and analogs thereof are also reported in EP O 473 268, published Mar. 4, 1992, entitled "Continuous Release Pharmaceutical Compositions Comprising a Polypeptide Covalently Conjugated To A Water Soluble Polymer," stating the use of various G-CSF and derivatives covalently conjugated to a water soluble particle polymer, such as polyethylene glycol.

A modified polypeptide having human granulocyte colony stimulating factor activity is reported in EP 0 335 423 published Oct. 4, 1989.

Another example is pegylated IL-6, EP 0 442 724, entitled, "Modified hIL-6," (see co-pending U.S. Ser. No. 07/632,070) which discloses polyethylene glycol molecules added to IL-6.

EP 0 154 316, published Sep. 11, 1985 reports reacting a lymphokine with an aldehyde of polyethylene glycol.

Many methods of attaching a polymer to a protein involve using a moiety to act as a linking group. Such moieties may, however, be antigenic. A tresyl chloride method involving no linking group is available, but this method may be difficult to use to produce therapeutic products as the use of tresyl chloride may produce toxic by-products. See Francis et al., In: Stability of protein pharmaceuticals: in vivo pathways of degradation and strategies for protein stabilization (Eds. Ahern., T. and Manning, M. C.) Plenum, N. Y., 1991) Also, Delgado et al., "Coupling of PEG to Protein By Activation With Tresyl Chloride, Applications In Immunoaffinity Cell Preparation", In: Fisher et al., eds., Separations Using Aqueous Phase Systems, Applications In Cell Biology and Biotechnology, Plenum Press, N.Y. N.Y., 1989 pp. 211–213.

Chamow et al., Bioconjugate Chem. 5: 133–140 (1994) report the modification of CD4 immuneadhesin with monomethoxlypoly (ethylene glycol) aldehyde via reductive alkylation. The authors resort that 50% of the CD4-Ig was MePEG-modified under conditions allowing the control over the extent of pegylation. Id. at page 137. The authors also report that the in vitro binding capability of the modified CD4-Ig (to the protein gp 120) decreased at a rate correlated to the extent of MePEGylation. Ibid. See also, Rose et al., Bioconjugate Chemistry 2: 154–159 (1991) which reports the selective attachment of the linker group carbohydrazide to the C-terminal carboxyl group of a protein substrate (insulin).

None of the methods in the general state of the art, or the art relating to particular proteins, allow for selective attachment of a water soluble polymer to the N-terminus of a protein such as G-CSF, however. Rather, the currently existing methods provide for non-selective attachment at any reactive group, whether located within the protein, such as a lysine side group, or at the N-terminus. This results in a heterogenous population. For example, for pegylated G-CSF molecules, some molecules have a different number of polyethylene glycol moieties than others. As an illustration, protein molecules with five lysine residues reacted in the above methods may result in a heterogenous mixture, some having six polyethylene glycol moieties, some five, some four, some three, some two, some one and some zero. And, among the molecules with several, the polyethylene glycol moieties may not be attached at the same location on different molecules.

This is disadvantageous when developing a therapeutic pegylated protein product. In such development, predictability of biological activity is crucial. For example, it has been shown that in the case of nonselective conjugation of superoxide dismutase with polyethylene glycol, several fractions of the modified enzyme were completely inactive (P. McGoff et al. Chem. Pharm. Bull. 36: 3079–3091 (1988)). One cannot have such predictability if the therapeutic protein differs in composition from lot to lot. Some of the polyethylene glycol moieties may not be bound as stably in some locations as others, and this may result in such moieties becoming dissociated with the protein. Of course, if such moieties are randomly attached and therefore become randomly dissociated, the pharmacokinetics of the therapeutic protein cannot be precisely predictable. From a consumer's point of view, the circulation time may vary from lot to lot, and thus dosing may be inaccurate. From a producer's point of view, garnering regulatory approval for sale of the therapeutic protein may have added complexities. Additionally, none of the above methods provide for selective N-terminal chemical modification without a linking moiety (between the protein and the polymer). If a linking moiety is used, there may be disadvantages due to possible antigenicity.

Thus, there exists a need for methods allowing for selectively N-terminally chemically modified proteins and analogs thereof, including G-CSF and consensus interferon (two chemically modified proteins exemplified below). The present invention addresses this need in a number of aspects.

SUMMARY OF THE INVENTION

The present invention relates to substantially homogenous preparations of N-terminally chemically modified proteins, and methods therefor. Unexpectedly, chemical modification at the N-terminus of G-CSF demonstrated advantages in stability which are not seen in other G-CSF species containing one chemical modification at another location on the molecule. Also unexpectedly, in the present process for making N-terminally chemically modified G-CSF, it was found that using reductive alkylation, one could provide conditions for selectively modifying the N-terminus, and this method is broadly applicable to other proteins (or analogs thereof), as well as G-CSF. Also surprisingly, using reductive alkylation, the end product—protein with an amine linkage to the water soluble polymer—was found to be far more stable than identical polymer/protein conjugate having an amide linkage. One other protein so modified (as described in a working example below) is consensus interferon. Thus, as described below in more detail, the present invention has a number of aspects relating to chemically modifying proteins (or analogs thereof) as well as specific modifications of specific proteins.

In one aspect, the present invention relates to a substantially homogenous preparation of N-terminally chemically modified G-CSF (or analog thereof) and related methods. One working example below demonstrates that N-terminally monopegylated G-CSF more stable than other types of monopegylated G-CSF. Additionally, since the N-terminus of the G-CSF molecule is more available during reaction with polyethylene glycol, a higher proportion of the N-termini are pegylated, and therefore, this species provides processing advantages.

The present invention also relates to a type of reductive alkylation which selectively activates α-amino group of the N-terminal residue of a protein or analog thereof, thereby providing for selective attachment of a water soluble polymer moiety at the N-terminus. This provides for a substantially homogenous preparation of polymer/protein conjugate molecules as well as (if polyethylene glycol is used) a preparation of pegylated protein molecules having the polyethylene glycol moiety directly coupled to the protein moiety. This method is described below for G-CSF and for consensus interferon, and these provide for additional aspects of the present invention.

BRIEF DESCRIPTION OF THE DRAWINGS

FIGS. 6A and 6B are the profiles for stability studies conducted at pH 6.0 at 4° C. for (6A) N-terminally monopegylated G-CSF or (6B) lysine 35 monopegylated G-CSF. FIG. 6C shows the profiles for extended stability studies at pH 6.0 and 4° C. for lysine 35 monopegylated G-CSF. Time ("T") indicates days.

DETAILED DESCRIPTION

Figure 1A:
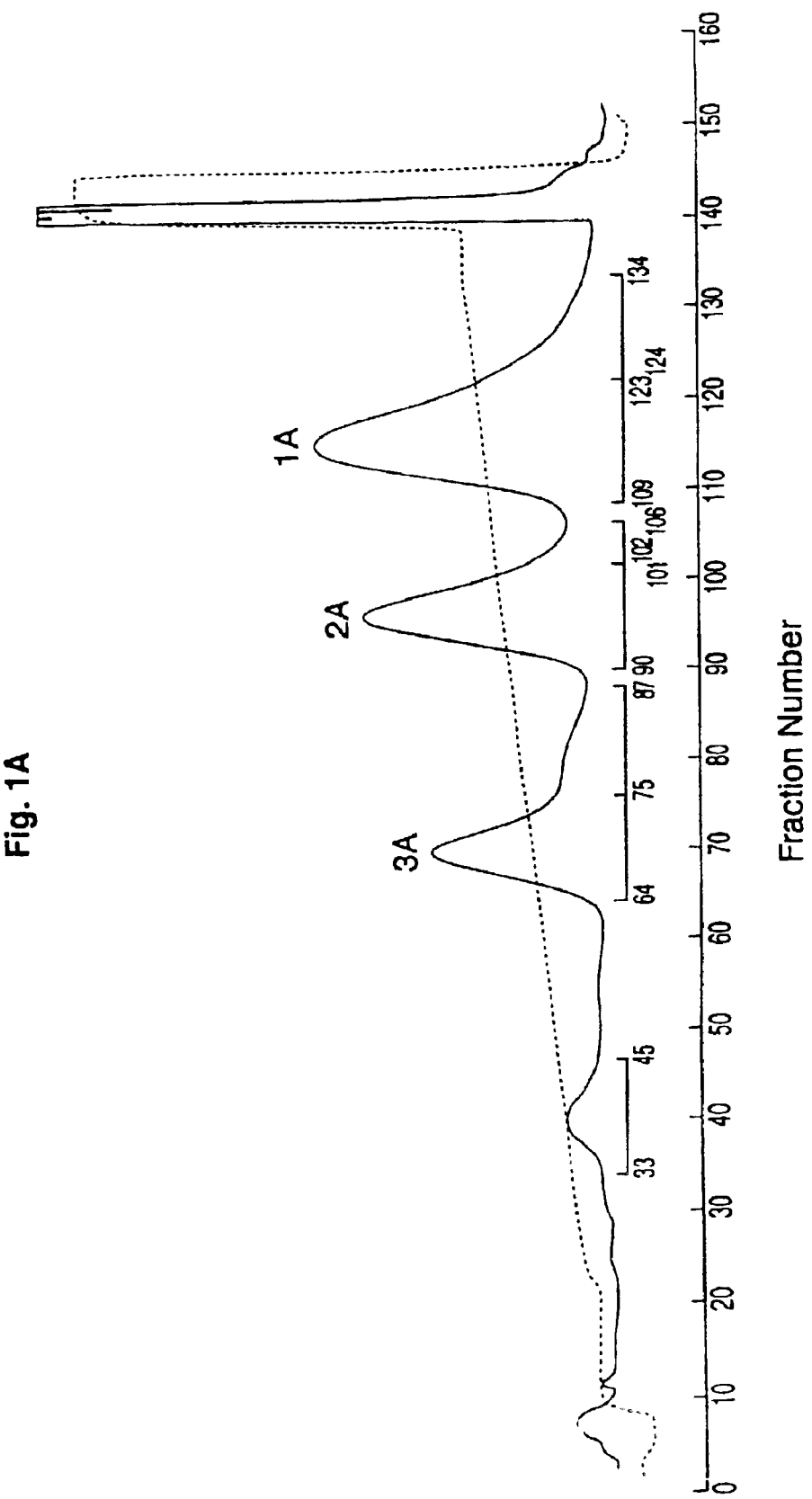
FIG. 1A is a reproduction of the chromatogram of the peaks from ion exchange chromatography of pegylated G-CSF.

The present invention relates to substantially homogenous preparations of N-terminally chemically modified proteins, and methods therefor.

In one aspect, the present invention relates to N-terminally chemically modified G-CSF compositions and methods therefor.

The present methods (for both N-terminally modified G-CSF as well as the present reductive alkylation methods) provide for a substantially homogenous mixture of monopolymer/protein conjugate. "Substantially homogenous" as used herein means that the only polymer/protein conjugate molecules observed are those having one polymer moiety. The preparation may contain unreacted (i.e., lacking polymer moiety) protein. As ascertained by peptide mapping and N-terminal sequencing, one example below provides for a preparation which is at least 90% monopolymer/protein conjugate, and at most 10% unreacted protein. Preferably, the N-terminally monopegylated material is at least 95% of the preparation (as in the working example below) and most preferably, the N-terminally monopegylated material is 99% of the preparation or more. The monopolymer/protein conjugate has biological activity. The present "substantially homogenous" N-terminally pegylated G-CSF preparations provided herein are those which are homogenous enough to display the advantages of a homogenous preparation, e.g., ease in clinical application in predictability of lot to lot pharmacokinetics.

One may choose to prepare a mixture of polymer/protein conjugate molecules, and the advantage provided herein is that one may select the proportion of monopolymer/protein conjugate to include in the mixture. Thus, if desired, one may prepare a mixture of various protein with various numbers of polymer moieties attached (i.e., di-, tri-, tetra-, etc.) and combine with the monopolymer/protein conjugate material prepared using the present methods, and have a mixture with a predetermined proportion of monopolymer/protein conjugate.

Provided below is a working example using G-CSF, which, as described above, is a therapeutic protein used to treat hematopoietic disorders. In general, G-CSF useful in the practice of this invention may be a form isolated from mammalian organisms or, alternatively, a product of chemical synthetic procedures or of prokaryotic or eukaryotic host expression of exogenous DNA sequences obtained by genomic or cDNA cloning or by DNA synthesis. Suitable prokaryotic hosts include various bacteria (e.g., *E. coli*); suitable eukaryotic hosts include yeast (e.g., *S. cerevisiae*) and mammalian cells (e.g., Chinese hamster ovary cells, monkey cells). Depending upon the host employed, the G-CSF expression product may be glycosylated with mammalian or other eukaryotic carbohydrates, or it may be non-glycosylated. The G-CSF expression product may also include an initial methionine amino acid residue (at position −1). The present invention contemplates the use of any and all such forms of G-CSF, although recombinant G-CSF, especially *E. coli* derived, is preferred, for, among other things, greatest commercial practicality.

Certain G-CSF analogs have been reported to be biologically functional, and these may also be chemically modified, by, for example, the addition of one or more polyethylene glycol molecules. G-CSF analogs are reported in U.S. Pat. No. 4,810,643. Examples of other G-CSF analogs which have been reported to have biological activity are those set forth in AU-A-76380/91, EP O 459 630, EP O 272 703, EP O 473 268 and EP O 335 423, although no representation is made with regard to the activity of each analog reportedly disclosed. See also AU-A-10948/92, PCT US94/00913 and EP 0 243 153.

Generally, the G-CSFs and analogs thereof useful in the present invention may be ascertained by practicing the chemical modification procedures as provided herein to selectively chemically modify the N-terminal α-amino group, and testing the resultant product for the desired biological characteristic, such as the biological activity assays provided herein. Of course, if one so desires when treating non-human mammals, one may use recombinant non-human G-CSF's, such as recombinant murine, bovine, canine, etc. See PCT WO 9105798 and PCT WO 8910932, for example.

Thus, another aspect of the present invention includes N-terminally chemically modified G-CSF analog compositions. As described above, G-CSF analogs may include those having amino acid additions, deletions and/or substitutions (as compared to the G-CSF amino acid sequence set forth in Example 1, below). Those G-CSF analogs which are predicted to function when N-terminally pegylated to selectively stimulate the production of neutrophils are those with an N-terminus which is not necessary for binding to a G-CSF receptor. See Hill et al., PNAS-USA 90: 5167–5171 (1993); see also PCT US94/00913.

The polymer molecules used may be selected from among water soluble polymers. (For the reductive alkylation procedure described herein, the polymers should have a single reactive aldehyde.) The polymer selected should be water soluble so that the protein to which it is attached does not precipitate in an aqueous environment, such as a physiological environment. For reductive alkylation, the polymer selected should have a single reactive aldehyde so that the degree of polymerization may be controlled as provided for in the present methods. The polymer may be branched or unbranched. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For G-CSF, these may be ascertained using the assays provided herein, and one skilled in the art should select the appropriate assays for other therapeutic proteins. The water soluble polymer may be selected from the group consisting of, for example, those listed above (in the Background section), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol.

Subject to considerations for optimization as discussed below, the polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight). Examples 1 and 2 below involve the use of PEG 6000, which was selected for ease in purification and for providing an adequate model system. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

One specific aspect of the present invention is N-terminally monopegylated G-CSF comprised of a polyethylene glycol moiety and a G-CSF moiety. For the present compositions, one may select from a variety of polyethylene glycol molecules (by molecular weight, branching, etc.), the proportion of polyethylene glycol molecules to G-CSF protein molecules in the reaction mix, the type of pegylation reaction to be performed, the method of obtaining the selected N-terminally pegylated G-CSF, and the type of G-CSF to be used. Further, the present compositions and methods include formulation of pharmaceutical compositions, methods of treatment and manufacture of medicaments.

The proportion of polyethylene glycol molecules to protein molecules will vary, as will their concentrations in the reaction mixture. In general, the optimum ratio (in terms of efficiency of reaction in that there is no excess unreacted protein or polymer) will be determined by the molecular weight of the polyethylene glycol selected. In addition, as one example of the present methods involves non-specific pegylation and later purification of N-terminally monopegylated species, the ratio may depend on the number of available reactive groups (typically $\alpha$ or $\epsilon$ amino groups) available. One working example herein involved a fairly low reaction ratio of protein: PEG molecules to obtain monopegylated material generally (1.5 PEG molecules per protein molecules).

For obtaining N-terminally pegylated G-CSF, the method for pegylation may also be selected from among various methods, as discussed above, or the present reductive alkylation as described in Example 2, below. A method involving no linking group between the polyethylene glycol moiety and the protein moiety is described in Francis et al., In: Stability of protein pharmaceuticals: in vivo pathways of degradation and strategies for protein stabilization (Eds. Ahern., T. and Manning, M. C.) Plenum, N. Y., 1991) Also, Delgado et al., "Coupling of PEG to Protein By Activation With Tresyl Chloride, Applications In Immunoaffinity Cell Preparation", In: Fisher et al., eds., Separations Using Aqueous Phase Systems, Applications In Cell Biology and Biotechnology, Plenum Press, N.Y.N.Y., 1989 pp. 211–213, involves the use of tresyl chloride, which results in no linkage group between the polyethylene glycol moiety and the protein moiety. This method may be difficult to use to produce therapeutic products as the use of tresyl chloride may produce toxic by-products. One of the present working examples involves the use of N-hydroxy succinimidyl esters of carboxymethyl methoxy polyethylene glycol. As will be discussed in more detail below, another working example involves the use of the present reductive alkylation methods.

The method of obtaining the N-terminally pegylated G-CSF preparation (i.e., separating this moiety from other monopegylated moieties if necessary) may be by purification of the N-terminally pegylated material from a population of pegylated G-CSF molecules. For example, presented below is an example where pegylated G-CSF is first separated by ion exchange chromatography to obtain material having a charge characteristic of monopegylated material (other multi-pegylated material having the same apparent charge may be present), and then the monopegylated materials are separated using size exclusion chromatography. In this way, N-terminally monopegylated G-CSF was separated from other monopegylated species, as well as other multi-pegylated species. Other methods are reported. For example, PCT WO 90/04606, published May 3, 1990, reports a process for fractionating a mixture of PEG-protein adducts comprising partitioning the PEG/protein adducts in a PEG-containing aqueous biphasic system.

In a different aspect, the present invention provides a method for selectively obtaining an N-terminally chemically modified protein (or analog). Provided below is a method of protein modification by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. The reaction is performed at pH which allows one to take advantage of the $pK_a$ differences between the $\epsilon$-amino groups of the lysine residues and that of the $\alpha$-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs.

Importantly, and surprisingly, the present invention provides for a method of making a substantially homogenous preparation of monopolymer/protein conjugate molecules, in the absence of further extensive purification as is required using other chemical modification chemistries. Additionally, the product having an amine linkage is unexpectedly more stable than a product produced with an amide linkage, and this is demonstrated in the aggregation studies below. More specifically, if polyethylene glycol is used, the present invention also provides for N-terminally pegylated protein lacking possibly antigenic linkage groups, and having the polyethylene glycol moiety directly coupled to the protein moiety without toxic by-products.

The reaction may be diagrammed as follows (indicating sodium cyanohydroboride as an illustrative reducing agent):

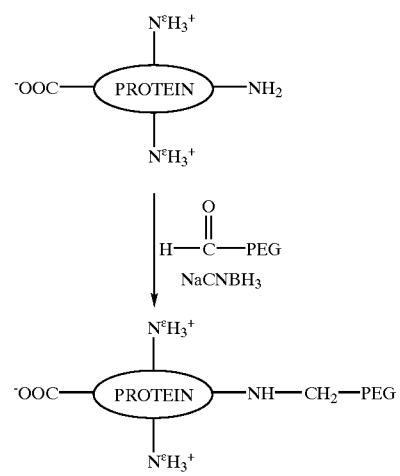

Thus, one aspect of the present invention is a method for preparing a polymer/protein conjugate comprised of (a) reacting a protein moiety having more than one amino group with a water soluble polymer moiety under reducing alkylation conditions, at a pH suitable to selectively activate the $\alpha$-amino group at the amino terminus of said protein moiety so that said water soluble polymer selectively attaches to said α-amino group; and (b) obtaining the reaction product. One may optionally, and preferably for a therapeutic product, separate the reaction products from unreacted moieties.

Another aspect of the present invention is that such reductive alkylation will provide for selective attachment of the polymer to any protein having an α-amino group at the amino terminus, and provide for a substantially homogenous preparation of monopolymer/protein conjugate. The term "monopolymer/protein conjugate" is used here to mean a composition comprised of a single polymer moiety attached to a protein moiety (also encompassed are those conjugates using protein analogs as described herein). The monopolymer/protein conjugate will have a polymer moiety located at the N-terminus, but not on amino side groups, such as those for lysine. The preparation will preferably be greater than 80% monopolymer/protein conjugate, and more preferably greater than 95% monopolymer protein conjugate.

For a substantially homogenous population of monopolymer/protein conjugate molecules, the reaction conditions are those which permit the selective attachment of the water soluble polymer moiety to the N-terminus of the desired protein. Such reaction conditions generally provide for $pK_a$ differences between the lysine amino groups and the α-amino group at the N-terminus (the pK being the pH at which 50% of the amino groups are protonated and 50% are not). In general, for different proteins, different pH's may be used for optimally modifying the α-amino groups of the N-terminus.

The pH also affects the ratio of polymer to protein to be used. In general, if the pH is lower than the pK, a larger excess of polymer to protein will be desired (i.e., the less reactive the N-terminal α-amino group, the more polymer needed to achieve optimal conditions). If the pH is higher than the pK, the polymer:protein ratio need not be as large (i.e., more reactive groups are available, so fewer polymer molecules are needed).

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

For the present reductive alkylation, the reducing agent should be stable in aqueous solution and preferably be able to reduce only the Schiff base formed in the initial process of reductive alkylation. Preferred reducing agents may be selected from the group consisting of sodium borohydride, sodium cyanoborohydride, dimethylamine borate, trimethylamine borate and pyridine borate. Sodium cyanoborohydride was used in the working examples below.

The water soluble polymer may be of the type described above, and should have a single reactive aldehyde for coupling to the protein. For polyethylene glycol, use of PEG 6000 for coupling to G-CSF and PEG 12000 for consensus interferon are described below. It is noted, that for G-CSF, PEG 12000, 20000 and 25000 have also been used successfully in the present methods. Polyethylene glycol propionaldehyde (see, e.g., U.S. Pat. No. 5,252,714) is advantageous for its stability in water.

As indicated above, the present methods are broadly applicable to any protein or analog thereof having an N-terminal α-amino group. For example, proteins which are the product of an exogenous DNA sequence expressed in bacteria may have, as a result of bacterially expression, an N-terminal methionyl residue with an α-amino group. As indicated above, peptides are included, as are peptidomimetics and other modified proteins. Protein analogs, such as the G-CSF analogs described above, and the non-naturally occurring consensus interferon are also suitable for the present methods.

Thus, for the present N-terminally chemically modified G-CSF, any of the G-CSF's or analogs as described herein may be used (e.g., those described supra). The working examples below use recombinant G-CSF produced in bacteria, having 174 amino acids and an extra N-terminal methionyl residue. As described herein, the chemical modification may be performed with any of the water soluble polymers described herein, and the present working examples describe the use of polyethylene glycol.

Consensus interferon is another protein used in the present working examples. Demonstrated below is the preparation of chemically modified consensus interferon using the present reductive alkylation methods for N-terminal monopegylation. Thus, other aspects of the present invention relate to these preparations. As employed herein, consensus human leukocyte interferon, referred to here as "consensus interferon," or "IFN-con", means a nonnaturally-occurring polypeptide, which predominantly includes those amino acid residues that are common to all naturally-occurring human leukocyte interferon subtype sequences and which include, at one or more of those positions where there is no amino acid common to all subtypes, an amino acid which predominantly occurs at that position and in no event includes any amino acid residue which is not extant in that position in at least one naturally-occurring subtype. IFN-con encompasses the amino acid sequences designated IFN-con$_1$, IFN-con$_2$ and IFN-con$_3$ which are disclosed in commonly owned U.S. Pat. Nos. 4,695,623 and 4,897,471, the entirety of which are hereby incorporated by reference. (U.S. Pat. Nos. 4,897,471 and 4,695,623 use the denomination "α" which is not used herein.) DNA sequences encoding IFN-con may be synthesized as described in the above-mentioned patents or other standard methods. IFN-con polypeptides are preferably the products of expression of manufactured DNA sequences, transformed or transfected into bacterial hosts, especially *E. coli*. That is, IFN-con is recombinant IFN-con. IFN-con is preferably produced in *E. coli* may be purified by procedures known to those skilled in the art and generally described in Klein et al., J. Chromatog. 454: 205–215 (1988) for IFN-con$_1$. Purified IFN-con may comprise a mixture of isoforms, e.g., purified IFN-con$_1$ comprises a mixture of methionyl IFN-con$_1$, des-methionyl IFN-con$_1$ and des-methionyl IFN-con$_1$ with a blocked N-terminus (Klein et al., Arc. Biochem. Biophys. 276: 531–537 (1990)). Alternatively, IFN-con may comprise a specific, isolated isoform. Isoforms of IFN-con are separated from each other by techniques such as isoelectric focusing which are known to those skilled in the art.

Thus, another aspect of the present invention is a chemically modified consensus interferon wherein said consensus interferon moiety is selected from the group consisting of IFN-con$_1$, IFN-con$_2$, and IFN-con$_3$. The chemical modification is using a water soluble polymer as described herein, such as PEG, and the present reductive alkylation methods may be used for selective N-terminal chemical modification. Example 3 herein illustrates a chemically modified IFN con$_1$ comprised of an IFN con$_1$ moiety connected at the N-terminus to a polyethylene glycol moiety (PEG 12000).

In another aspect, the present methods yield pegylated proteins where the polyethylene glycol moiety is directly attached to a protein moiety, and a separate linking group is absent and no toxic by-products are present. The examples include G-CSF and consensus interferon as described herein. For a population of pegylated G-CSF protein molecules wherein the polyethylene glycol moiety is directly attached to the G-CSF protein moiety (not necessarily a population of N-terminally pegylated G-CSF molecules), one may perform the above reductive alkylation with or without an acidic pH.

In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of monopolymer/protein conjugate products of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Such compositions may influence the physical state, stability, rate of in vivo release, and rate of in vivo clearance of the present N-terminally chemically modified proteins. See, e.g., Remington's Pharmaceutical Sciences, 18th Ed. (1990, Mack Publishing Co., Easton, Pa. 18042) pages 1435–1712 which are herein incorporated by reference.

In yet another aspect of the present invention, methods of treatment and manufacture of a medicament are provided. Conditions alleviated or modulated by the administration of the present polymer/G-CSF conjugates (or analogs having the hematopoietic biological properties of naturally occurring G-CSF) are typically those characterized by a reduced hematopoietic or immune function, and, more specifically, a reduced neutrophil count. Such conditions may be induced as a course of therapy for other purposes, such as chemotherapy or radiation therapy. Such conditions may result from infectious disease, such as bacterial, viral, fungal or other infectious disease. For example, sepsis results from bacterial infection. Or, such condition may be hereditary or environmentally caused, such as severe chronic neutropenia or leukemias. Age may also play a factor, as in the geriatric setting, patients may have a reduced neutrophil count or reduced neutrophil mobilization. Some of such conditions are reviewed in Filgrastim (r-met Hu G-CSF) in Clinical Practice, Morstyn, G. and T. M. Dexter, eds., Marcel Dekker, Inc., N.Y., N.Y. (1993), 351 pp. Other less-studied conditions which may be alleviated or modulated by administration of the present polymer/G-CSF conjugates may include the reduction of lipids (or cholesterol) in the blood stream, and certain cardiovascular conditions, as G-CSF may induce production of plasminogen activators. The mode of action of G-CSF (or analogs) in these settings is not well understood at present. The addition of a water soluble polymer, such as polyethylene glycol, may provide practical patient benefits in that the sustained duration of biological activity may allow for fewer G-CSF injections per course of treatment.

Generally, conditions which may be alleviated or modulated by administration of the present polymer/consensus interferon are those to which consensus interferon is applicable and include cell proliferation disorders, viral infections, and autoimmune disorders such as multiple sclerosis. Cf., McManus Balmer, DICP, The Annals of Pharmacotherapy 24: 761–767 (1990)(Clinical use of biologic response modifiers in cancer treatment: an overview. Part I. The Interferons). Methods and compositions for the treatment of cell proliferation disorders using consensus interferon are described in PCT WO 92/06707, published Apr. 30, 1992, which is herein incorporated by reference. For example, hepatitis (A, B, C, D, E) may be treatable using the present pegylated consensus interferon molecules. The working example below demonstrates that, in vitro, chemically modified consensus interferon has 20% of the biological activity of non-chemically modified consensus interferon.

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. Generally, for injection or infusion, dosage will be between 0.01 $\mu$g/kg body weight, (calculating the mass of the protein alone, without chemical modification), and 100 $\mu$g/kg (based on the same).

The below examples illustrate the various aspects discussed above. In Example 1, the advantages of N-terminally pegylated G-CSF are demonstrated as compared to G-CSF monopegylated at lysine-35 or lysine 41 (of the G-CSF met+174 amino acid version). Example 2 illustrates she present reductive alkylation in N-terminally pegylating G-CSF. The method provides for a substantially homogenous preparation of N-terminally pegylated G-CSF. Example 3 illustrates the present reductive alkylation in N-terminally pegylating consensus interferon.

EXAMPLE 1

A. Preparation of Recombinant Human Met-G-CSF

Recombinant human met-G-CSF (referred to as "rhG-CSF" or "r-met-hu-G-CSF" from time to time herein) was prepared as described above according to methods in the Souza patent, U.S. Pat. No. , 4,810,643, which is herein incorporated by reference. The rhG-CSF employed was an E. coli derived recombinant expression product having the amino acid sequence (encoded by the DNA sequence)

```
ATG ACT CCA TTA GGT CCT GCT TCT TCT CTG CCG CAA AGC TTT CTG
 M   T   P   L   G   P   A   S   S   L   P   Q   S   F   L

CTG AAA TGT CTG GAA CAG GTT CGT AAA ATC CAG GGT GAC GGT GCT
 L   K   C   L   E   Q   V   R   K   I   Q   G   D   G   A

GCA CTG CAA GAA AAA CTG TGC GCT ACT TAC AAA CTG TGC CAT CCG
 A   L   Q   E   K   L   C   A   T   Y   K   L   C   H   P
```

-continued

```
GAA GAG CTG GTA CTG CTG GGT CAT TCT CTT GGG ATC CCG TGG GCT
 E   E   L   V   L   L   G   H   S   L   G   I   P   W   A

CCG CTG TCT TCT TGT CCA TCT CAA GCT CTT CAG CTG GCT GGT TGT
 P   L   S   S   C   P   S   Q   A   L   Q   L   A   G   C

CTG TCT CAA CTG CAT TCT GGT CTG TTC CTG TAT CAG GGT CTT CTG
 L   S   Q   L   H   S   G   L   F   L   Y   Q   G   L   L

CAA GCT CTG GAA CGT ATC TCT CCG GAA CTG GGT CCG ACT CTG GAC
 Q   A   L   E   G   I   S   P   E   L   G   P   T   L   D

ACT CTG GAG CTA GAT GTA GCT GAC TTT GCT ACT ACT ATT TGG CAA
 T   L   Q   L   Q   V   A   Q   F   A   T   T   I   W   Q

CAG ATG GAA GAG CTC GGT ATG GCA CCA GCT CTG CAA CCG ACT CAA
 Q   M   E   E   L   G   H   A   P   A   L   Q   P   T   Q

GGT GCT ATG CCG GCA TTC GCT TCT GCA TTC CAG CGT CGT GCA GGA
 G   A   H   P   A   F   A   S   A   F   Q   R   R   A   G

GGT GTA CTG GTT GCT TCT CAT CTG CAA TCT TTC CTG GAA GTA TCT
 G   V   L   V   A   S   H   L   Q   S   F   L   E   V   S

TAC CGT GTT CTG CGT CAT CTG GCT GAG CCG TAA TAG
 Y   R   V   L   R   H   L   A   Q   P   *   *
```

(This was also the non-pegylated composition used for the control animals.) Alternatively one may use purchased Neupogen® for the following pegylation procedures (the package insert for which is herein incorporated by reference).

B. Preparation of Pegylated G-CSF

A 10 mg/ml solution of the above rh-G-CSF, in 100 mM Bicine pH 8.0, was added to solid SCM-MPEG (N-hydroxy succinimidyl esters of carboxymethyl methoxy polyethylene glycol) (Union Carbide) with an average molecular weight of 6000 Daltons. This gave a 1.5 molar excess of SCM-MPGE to rh-G-CSF. After one hour with gentle stirring, the mixture was diluted to 2 mg/ml with sterile water, and the pH was adjusted to 4.0 with dilute HCl. The reaction was carried out at room temperature. At this stage, the reaction mixture consisted mainly of three forms of mono-pegylated rh-G-CSF, some di-pegylated rh-G-CSF, unmodified rh-G-CSF and reaction bi-product (N-hydroxy succinimide).

C. Preparation of N-terminally Pegylated rh-G-CSF

The three forms of monopegylated rh-G-CSF were separated from each other using ion exchange chromatography. The reaction mixture was loaded (1 mg protein/ml resin) onto a Pharmacia S Sepharose FF column (Pharmacia XK50/30 reservoir, bed volume of 440 ml) equilibrated in buffer A (20 mM sodium acetate, pH 4.0). The column was washed with 3 column volumes of buffer A. The protein was eluted using a linear gradient from 0–23% buffer B (20 mM sodium acetate, pH 4.0, 1M NaCl) in 15 column volumes. The column was then washed with one column volume of 100% buffer B and reequilibrated with 3 column volumes of buffer A. The flow rate for the entire run was maintained at 8 ml/min. The eluent was monitored at 280 nm and 5 ml fractions were collected. Fractions containing the individual monopegylated species were pooled according to FIG. 1A. These pools were concentrated with a 350 mL Amicon stirred cell using a YM10 76 mm membrane.

Pooled fractions from the ion exchange chromatography were subjected to size exclusion chromatography to separate di-pegylated species from monopegylated species. Typically, 5–10 mg in 2–5 ml of solution were loaded onto a 120 ml Pharmacia Superdex 75 HR 16/60 column equilibrated with 20 mM sodium acetate pH 4.0. The column was run at 1.5 ml/min for 100 min. Two ml fractions were collected. The protein content of the eluent was monitored at 280 nm. Fractions from separated peaks were pooled and subjected to analysis. The table below compares the proportional yields for each peak.

TABLE 1

Relative Yields and Site of Modification

| Site of Modification | FIG. 1A Reference | Relative Yields |
|---|---|---|
| N-Terminus | Peak 1A | 3 |
| Lysine-35 | Peak 2A | 2 |
| Lysine-41 | Peak 3A | 1 |

Under these conditions, the lysines at positions 17 and 24 probably were not significantly pegylated.

D. Characterization

Figure 1B:
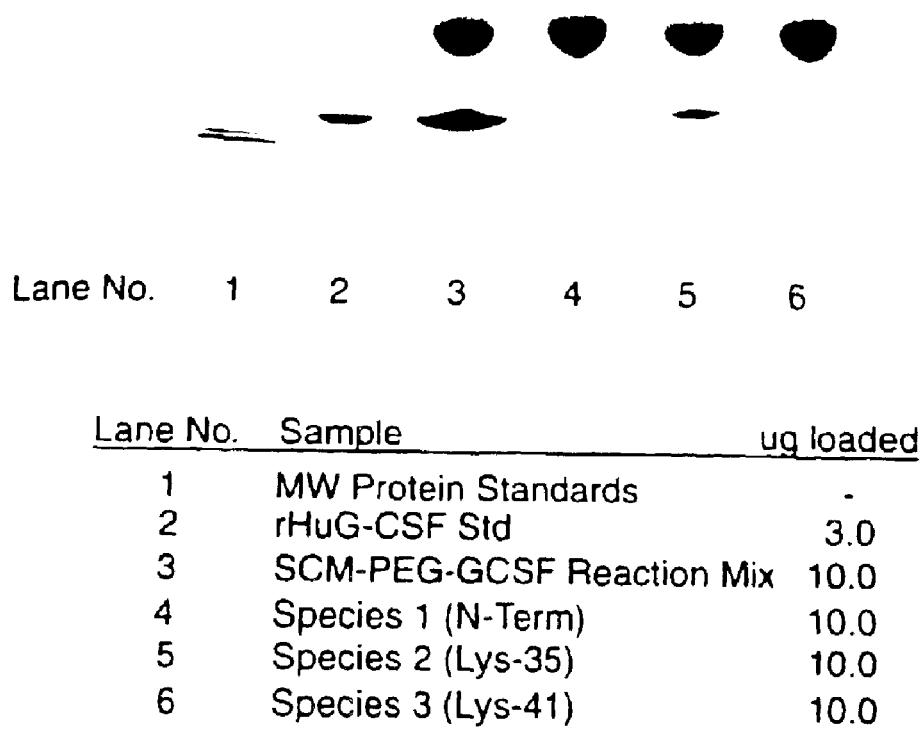
FIG. 1B is an SDS-PAGE of various species of monopegylated G-CSF.
Figure 3A:
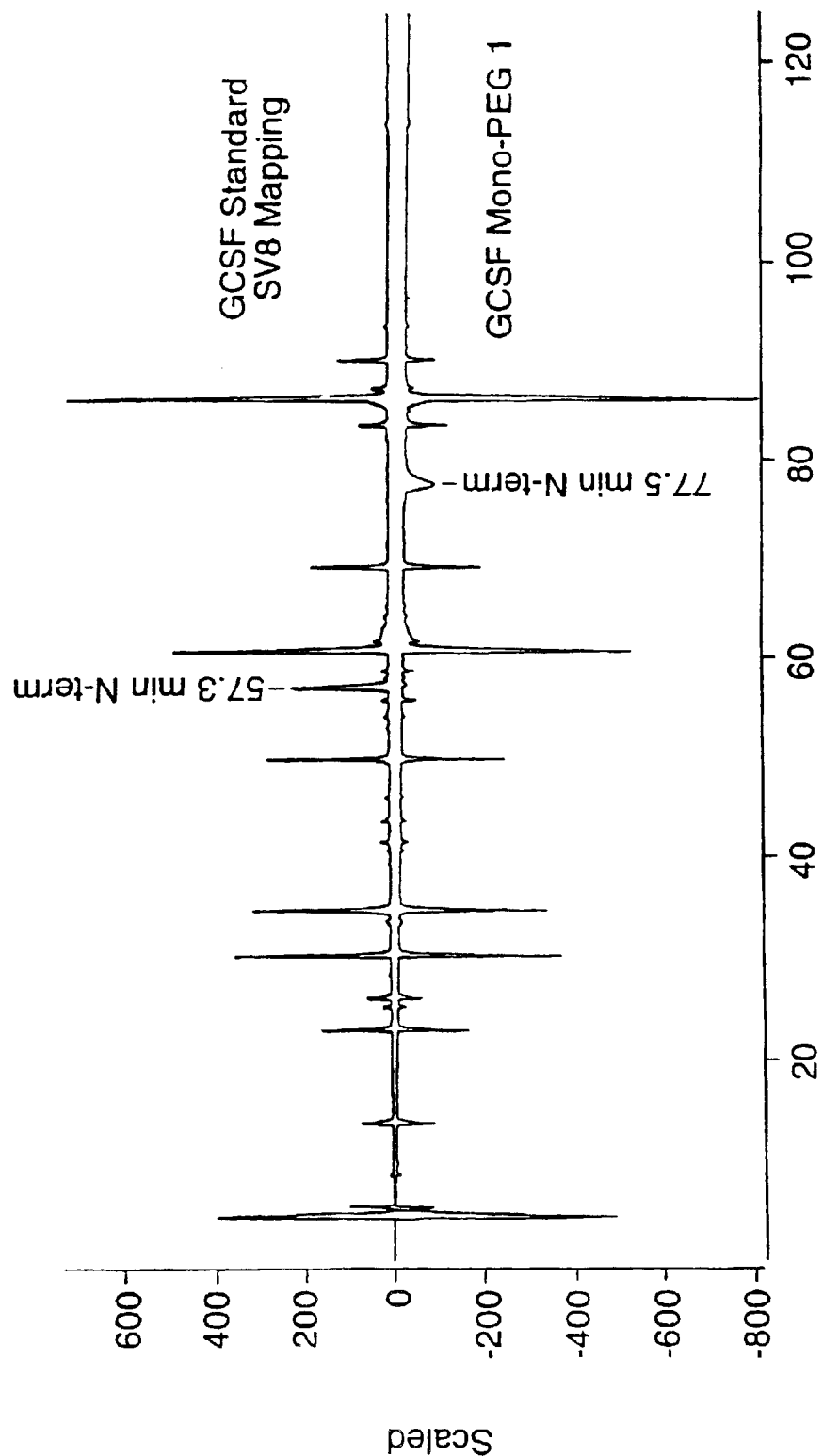
FIGS. 3A, 3B, and 3C are HPLC endoproteinase SV8 peptide mapping tracings of (3A) N-terminally pegylated G-CSF; (3B) lysine 35 monopegylated G-CSF; (3C) lysine 41 monopegylated G-CSF.
Figure 3B:
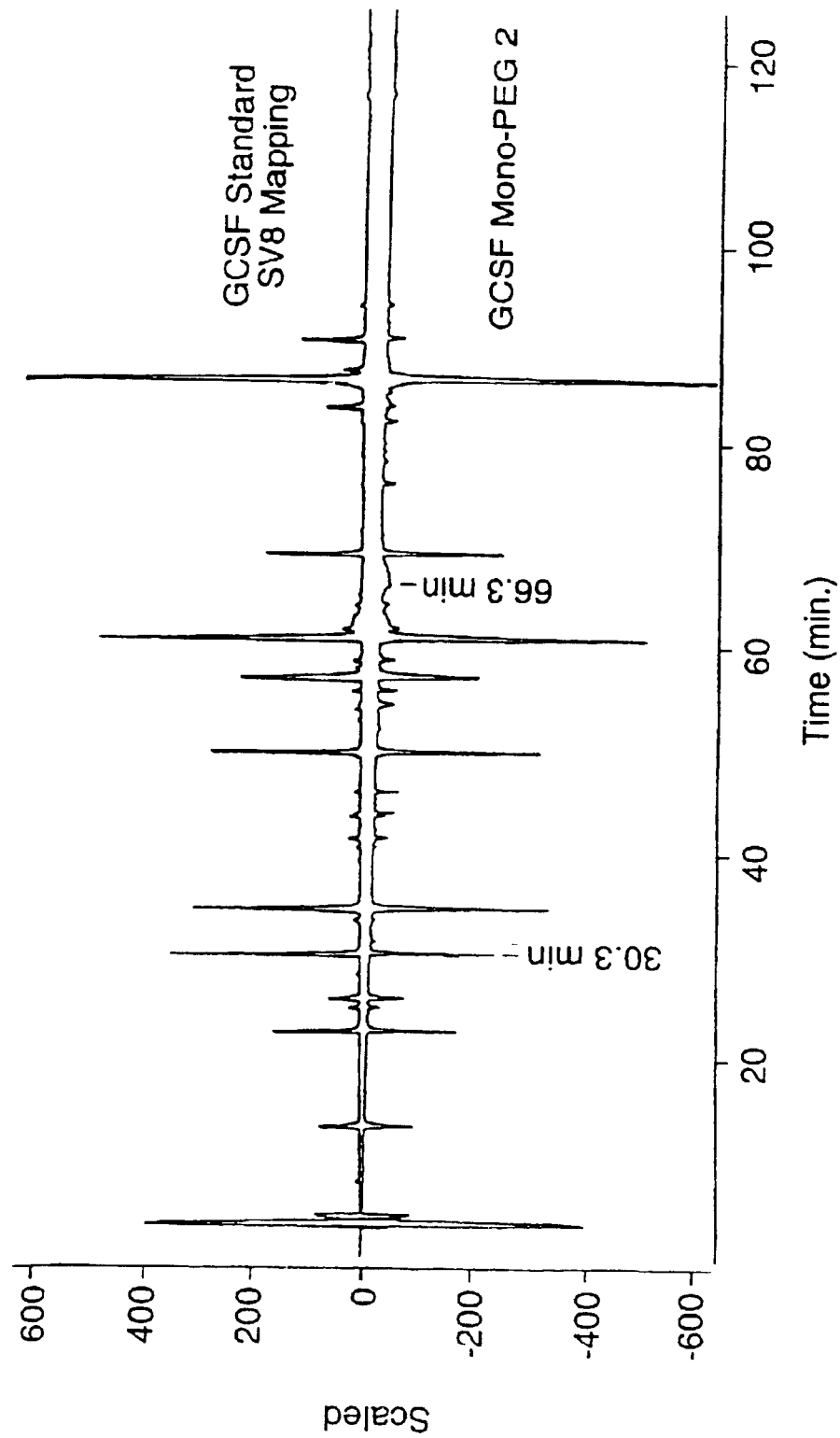
Figure 3C:
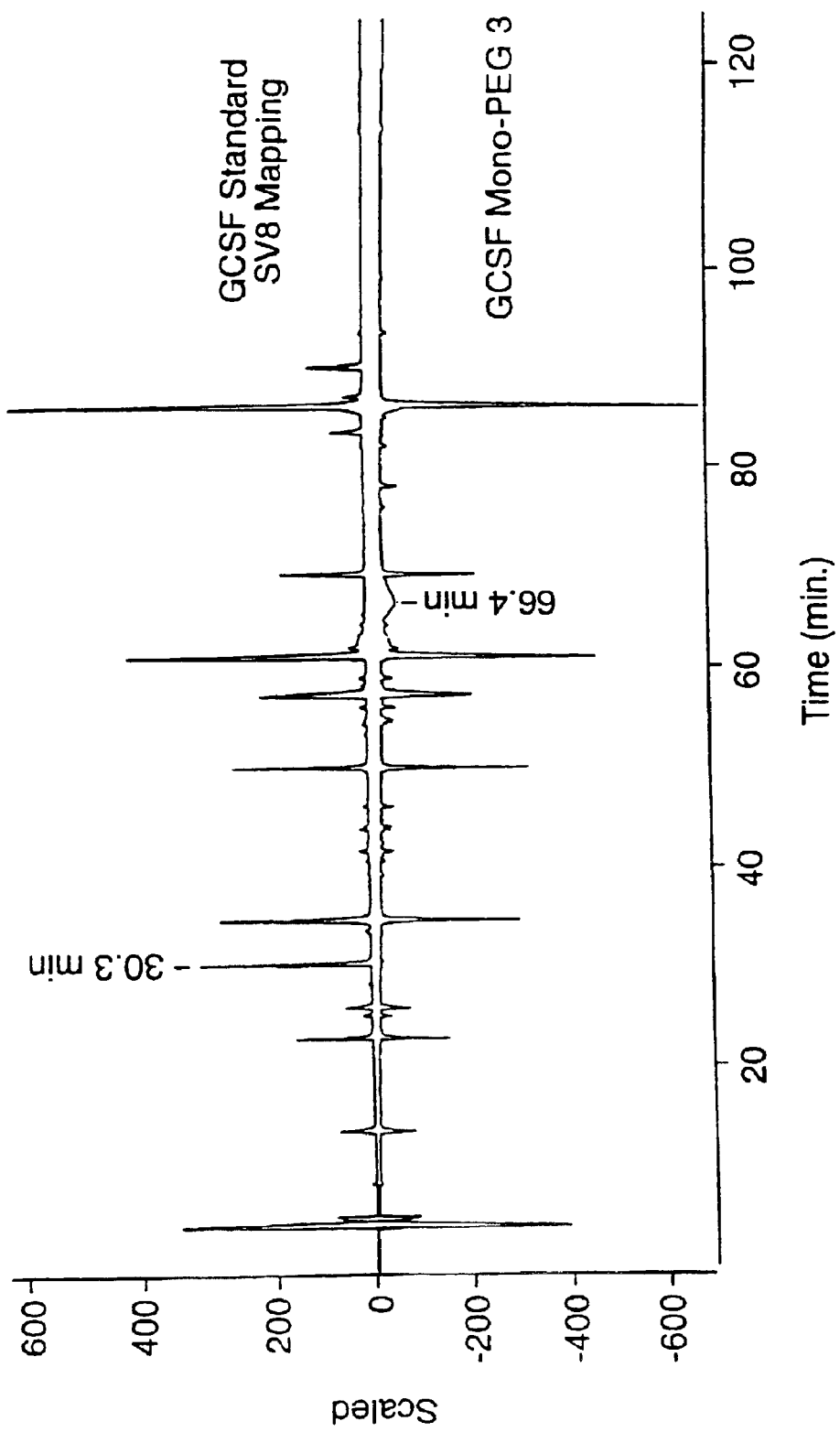
Figure 4:
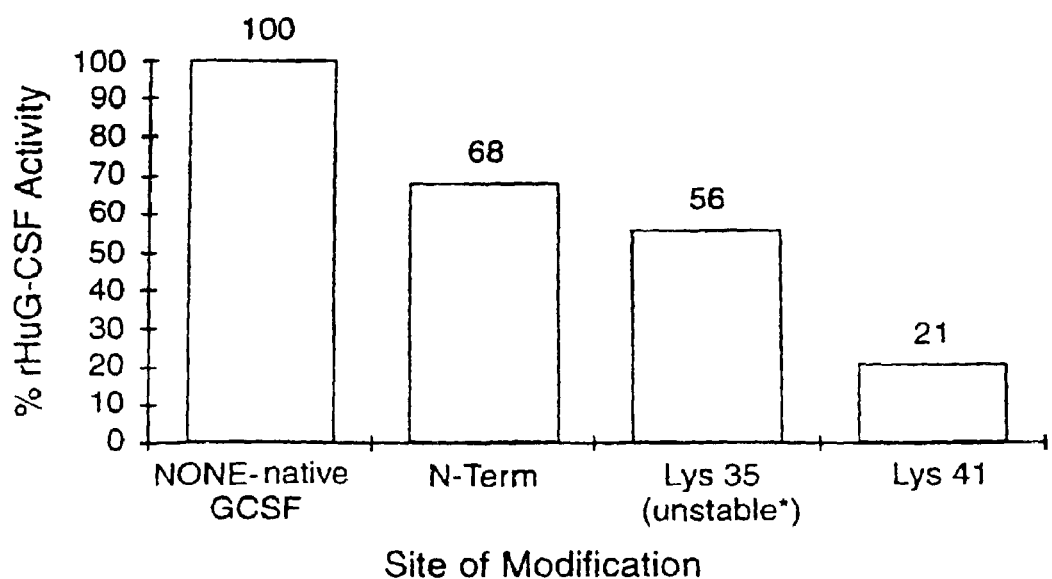
FIG. 4 is a bar graph illustrating a comparison of in vitro bioactivity of monopegylated G-CSF species compared to an unpegylated standard.
Figure 5A:
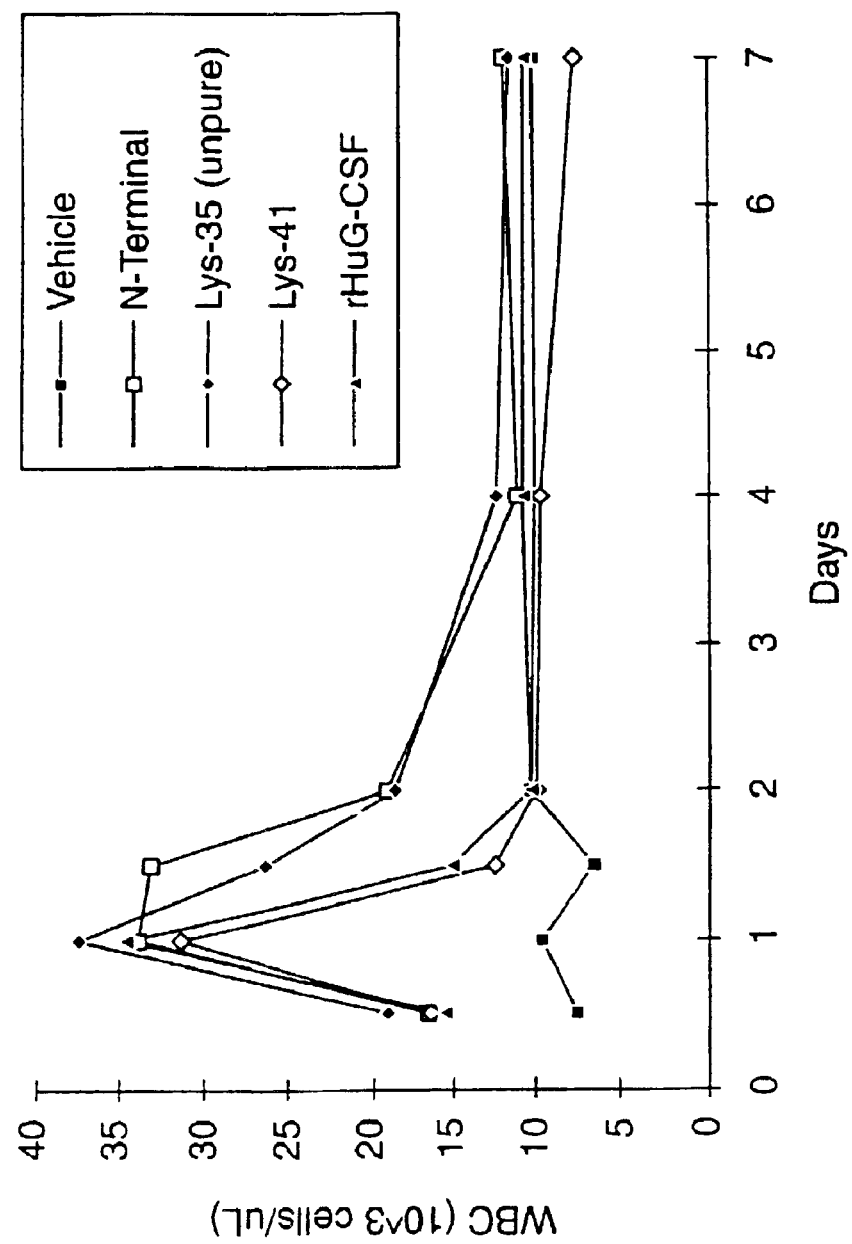
FIGS. 5A and 5B are graphs illustrating results of in vivo bioactivity assays of monopegylated G-CSF derivatives, with 5A illustrating the average hamster white blood cell count after a single subcutaneous injection of N-terminally pegylated G-CSF, lysine 35 monopegylated G-CSF, or lysine 41 monopegylated G-CSF, and 5B illustrating the net average white blood cell count area under the curve after a single subcutaneous injection of the various monopegylated G-CSF derivatives listed above.
Figure 5B:
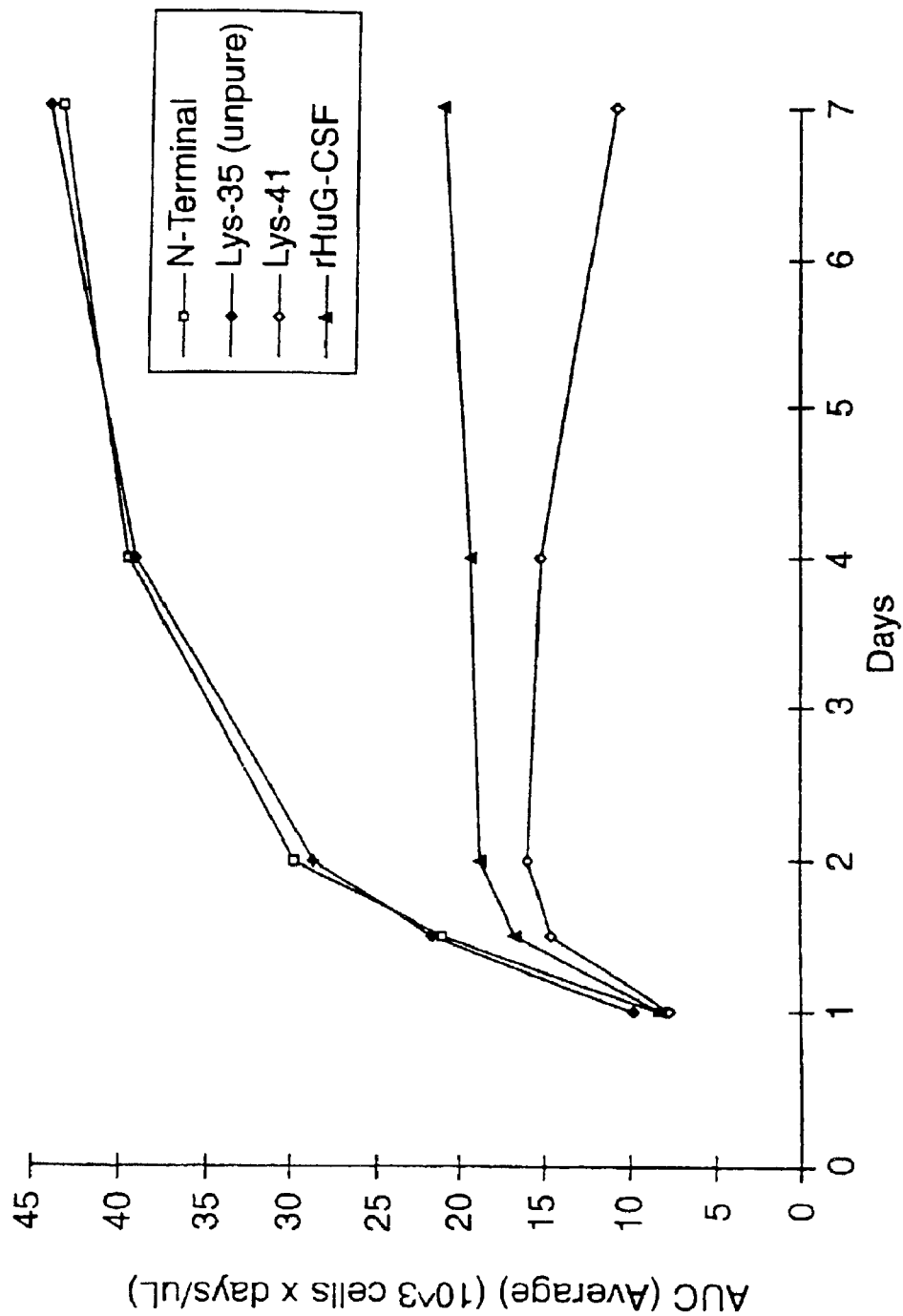

Five analyses were done to characterize each sample: (1) SDS-Page (FIG. 1B), (2) Size exclusion chromatography HPLC ("SEC HPLC")(FIG. 2), (3) peptide mapping analysis (FIGS. 3A, 3B, and 3C), (4) in vitro G-CSF bioassay (FIG. 4), and (5) in vivo testing in hamster (FIGS. 5A and 5B).

With regard to the composition of each sample, results demonstrate that, of the N-terminally monopegylated G-CSF, the samples showed a greater than 95% N-terminally pegylated composition, with the remainder probably being unpegylated material (although the remainder of the samples is lower than the detection limit of the assay). With regard to the percent monopegylated for each of the three types of monopegylated material (N-terminal, pegylated at lysine 35, and pegylated at lysine 41), the N-terminal and the lysine 41 demonstrated greater than 97% monopegylated, and the lysine 35 pegylated material being somewhat lower, probably due to the instability of the molecule in the assay conditions. To summarize, the following results were obtained:

TABLE 2

Percent Composition of
N-terminally pegylated G-CSF

|  | Non-Reduced SDS PAGE | SEC HPLC | N-Terminal Sequencing* |
| --- | --- | --- | --- |
| Mono-pegylated G-CSF | 97.44 | 99.43 | 96.6 |
| Unmodified G-CSF | 2.56 | 0.57 | 3.4 |

*The N-terminal sequencing, as discussed infra is not here considered quantitative, as there may have been artifactual separation of the polyethylene glycol molecule from the N-terminus of the protein during the sequencing process.

TABLE 3

Percent Monopegylated for Three Species

|  | N-terminal PEG-GCSF (RI/UV = .96)* | LYS35 PEG-GCSF** (RI/UV = .72) | LYS41 PEG-GCSF (RI/UV = 1.12) |
| --- | --- | --- | --- |
| Non-reduced |  |  |  |
| SDS-PAGE | 97.44 | 77.41 | 100.00 |
| SEC HPLC | 99.43 | 93.38 | 99.96 |

*RI/UV refers to the Index of Refraction/Ultraviolet light absorbance ratio, and is used to estimate the number of polyethylene glycol molecules per molecule of protein. It is calculated from the SEC HPLC data using an Index of Refraction for polyethylene glycol and an ultraviolet absorbance for protein.
**Note that this species is unstable under the assay conditions used.

Methods

1. SDS-PAGE. SDS-PAGE was carried out in a non-reduced 4–20% ISS Daiichi Pure Chemicals, Co., Tokyo, Japan minigel using a Coomassie Brillant Blue R-250 stain. The gel was scanned using a molecular Dynamics Densitometer with Image Quant. Results: Results are presented in FIG. 1B. Lane number 1 (from the left hand side) included molecular weight protein standards (Novex Mark 12 Molecular Weight Standards). Lane 2 contains 3 µg rh-G-CSF standard. Lane 3 contains the SCM-PEG-GCSF reaction mix, with 10 µg loaded. Lane 4 contains N-terminally monopegylated G-CSF, with 10 µg loaded. Lane 5 contains 10 µg of monopegylated G-CSF with the pegylation site at the lysine found at the 35th residue from the N-terminal methionine. Lane 6 contains 10 µg of monopegylated G-CSF with the pegylation site at the lysine found at the 41st residue from the N-terminal methionine. As can be seen, Lane 3, containing the N-terminally monopegylated material, shows a single band 2. Size Exclusion Chromatography-High Pressure Liquid Chromatography. SEC-HPLC was carried out using a Waters HPLC system with a Biosep SEC 3000 column, using 100 mM sodium phosphate, pH 6.9, 1 ml/min for 20 minutes. The signal was monitored at 280 nm. Results: As can be seen from FIG. 2, line "C," containing the N-terminally monopegylated rh-G-CSF contains a single peak, as do lines "D" (Lys-35 monopegylated material) and "E" (Lys-41 monopegylated material). This indicates substantial purity among the separated fractions of monopegylated G-CSF.

3. Peptide mapping. The following methods were used. Three samples, called "Mono-PEG 1", "Mono-PEG-2", and "Mono-PEG-3", were analyzed. (a) Reductive alkylation. 500 µg aliquots of mono-PEG G-CSF were speed vac dried and reconstituted to a concentration of 1 mg in 950 µl in 0.3 M Tris-HCl containing 6 M Guanidinum HCl and 1 mM EDTA pH 8.4. Samples were then S-carboxymethylated by adding iodoacetic acid and incubated at 37° C. for 20 minutes. Samples were then desalted using Sephadex G-25 Quick Spin Protein Columns and buffer exchanged. After desalting and buffer exchange, sample concentration was adjusted to 0.5 mg/ml using additional buffer. (b) Endoproteinase SV8 digestion. Samples were digested with SV8 (enzyme to substrate ratio of 1:25) at 25° C. for 26 hours. (c) HPLC peptide mapping. Protein digests were injected onto a Vydac C4 column (4.6×250 mm, 5µ particle size, 300 Å pore size) and peptides were mapped by HPLC using a linear gradient of acetonitrile in 0.1% TFA. Peptides were manually collected and dried in a Speed Vac for sequence analysis. Results: As compared to a reference standard, (i) (FIG. 3A) for "Mono-PEG-1", (the N-terminally mono-pegylated material), a peak at 57.3 minutes diminished and a new peak appeared at 77.5 minutes; (ii) (FIG. 3B) for "Mono-PEG-2", (the lysine 35 pegylated material), there was a decrease in peak height for a peptide with a retention time of 30.3 minutes, and a new peak eluted at 66.3 minutes; (iii) (FIG. 3C) for "Mono-PEG-3" (the lysine 41 pegylated material), the peak at retention time of 30.3 minutes was missing, and a new peak appeared at 66.4 minutes. These peptides were the only significant differences in the sample maps. There were some small incomplete cleavages seen on either side of the peptide at 86.1 minutes due to minor digestion differences. (d) N-terminal sequence analysis. Each of the "new" peptides in the above maps were N-terminally sequenced for identification. The dried peptides were reconstituted in 0.1% TFA and sequenced on an ABI protein sequencer. For "Mono-PEG-1" (the N-terminally pegylated material), 60% of the "new" peak (at 77.5 minutes) was sequenced for 10 cycles. The initial yield was less than 5%, indicating that the N-terminal methionyl residue is blocked by a polyethylene glycol molecule. It is noted that this initial peptide should have resulted in a zero initial yield, and the <5% yield observed may be from detachment of the polyethylene glycol from the N-terminal methionyl during sequence analysis. The sequence detected was that of the N-terminal peptide, M-T-P-L-G-P-A-S-S. For "Mono-PEG-2", (the lysine 35 pegylated material), 80% of the total peak volume was collected for the peak at 66.3 minutes, and was sequenced for 9 cycles. The recovery of lysine 35 was significantly low, indicating pegylation at position 35. The recovery of lysine 41 was consistent with the other residue, indicating no modification of this position. The peptide at 30.3 minutes decreased in peak height compared to the corresponding peak in the standard reference map. The peptide at 30.3 minutes is only 57.5% of the peak area of the corresponding peptide. The sequence detected for this species was K-L-C-A-T-Y-K-L. For "Mono-PEG-3", the lysine 41 material, 80% of the total peak volume collected for the peptide eluting at 66.4 minutes was sequenced for 9 cycles. The sequence detected was K-L-C-A-T Y-K-L, and contained lysine residues 35 and 41. The recovery of lysine 35 was consistent with other residue recoveries. The recovery of lysine 41 was significantly lower indicating pegylation at position 41. Results: "Mono-PEG-1" is N-terminally monopegylated material; "Mono-PEG-2" is lysine 35 partially pegylated; and "Mono-PEG-3" is lysine 41 pegylated material. By comparing both the reference standard (non-pegylated G-CSF) and GCSF monopegylated 1, 2, and 3 peptide maps, it was found that both the "Mono-PEG-2" (lysine 35) and "Mono-PEG-3" (lysine 41) maps exhibit slightly diminished peak heights for the N-terminal peptide. This indicates that the lysine 35 and lysine 41 material contains a small amount of N-terminally pegylated material or that the N-terminal methionine has a small percentage of pegylation.

4. In vitro activity. The material was active. FIG. 4 illustrates the results of in vitro assays. As can be seen, the N-terminally monopegylated material had 68% of the activity of non-modified rhG-CSF. Methods: The G-CSF in vitro bioassay is a mitogenic assay utilizing a G-CSF dependent clone of murine 32D cells. Cells were maintained in Iscoves medium containing 5% FBS and 20 ng/ml rhG-CSF. Prior to sample addition, cells were prepared by rinsing twice with growth medium lacking rhG-CSF. An extended twelve point rhG-CSF standard curve was prepared, ranging from 48 to 0.5 ng/ml (equivalent to 4800 to 50 IU/ml). Four dilutions, estimated to fall within the linear portion of the standard curve, (1000 to 3000 IU/ml), were prepared for each sample and run in triplicate. Because of their apparent lower activity in vitro, the pegylated rhG-CSF samples were diluted approximately 4–10 times less. A volume of 40 $\mu$l of each dilution of sample or standard is added to appropriate wells of a 96 well microtiter plate containing 10,000 cells/well. After forty-eight hours at 37° C. and 5.5% $CO_2$, 0.5 $\mu$mCi of methyl-$^3$H-thymidine was added to each well. Eighteen hours later, the plates were then harvested and counted. A dose response curve (log rhG-CSF concentration vs. CPM-background) was generated and linear regression analysis of points which fall in the linear portion of the standard curve was performed. Concentrations of unknown test samples were determined using the resulting linear equation and correction for the dilution factor. Results: Results are presented in FIG. 4. As can be seen, of the three monopegylated species, N-terminally monopegylated G-CSF demonstrates the highest in vitro biological activity.

5. In vivo activity. In vivo testing confirmed the activity of the N-terminally pegylated material. The in vivo testing was carried out by dosing male golden hamsters with a 0.1 mg/kg of sample, using a single subcutaneous injection. Four animals were subjected to terminal bleeds per group per time point. Serum samples were subject to a complete blood count on the same day that the samples were collected. The average white blood cell counts were calculated. As can be seen in FIGS. 5A and 5B, the response from each material peaks after one day following a single subcutaneous injection of 0.1 mg/kg. Two of the monopegylated materials, (N-terminal and Lys-35) showed prolonged responses, while the response for the protein pegylated at lysine-41 showed no increase in in vivo activity over unmodified rhG-CSF (indeed it shows less, FIG. 5B ). These results illustrate that attaching a single polyethylene glycol molecule can dramatically alter the therapeutic profile of a protein and that the benefit of pegylating a protein can be dependent upon the site of modification. (The net average WBC area under the curve after the single subcutaneous injection (calculated according to CRC Standard Mathematical Tables, 26th Ed. (Beyer, W. H., Ed.) CRC Press Inc., Boca Raton, Fla. 1981. p. 125) was similar for the Lys-35 and N-terminal monopegylated species.)

E. Stability Studies

In addition, stability studies were performed on the N-terminal and Lys-35 monopegylated species as prepared above. (The Lys-41 material was not used as it demonstrated no additional activity beyond unmodified G-CSF). These studies demonstrate that the N-terminally pegylated G-CSF is unexpectedly more stable upon storage than the other form of monopegylated G-CSF, monopegylated lysine 35.

Figure 6A:
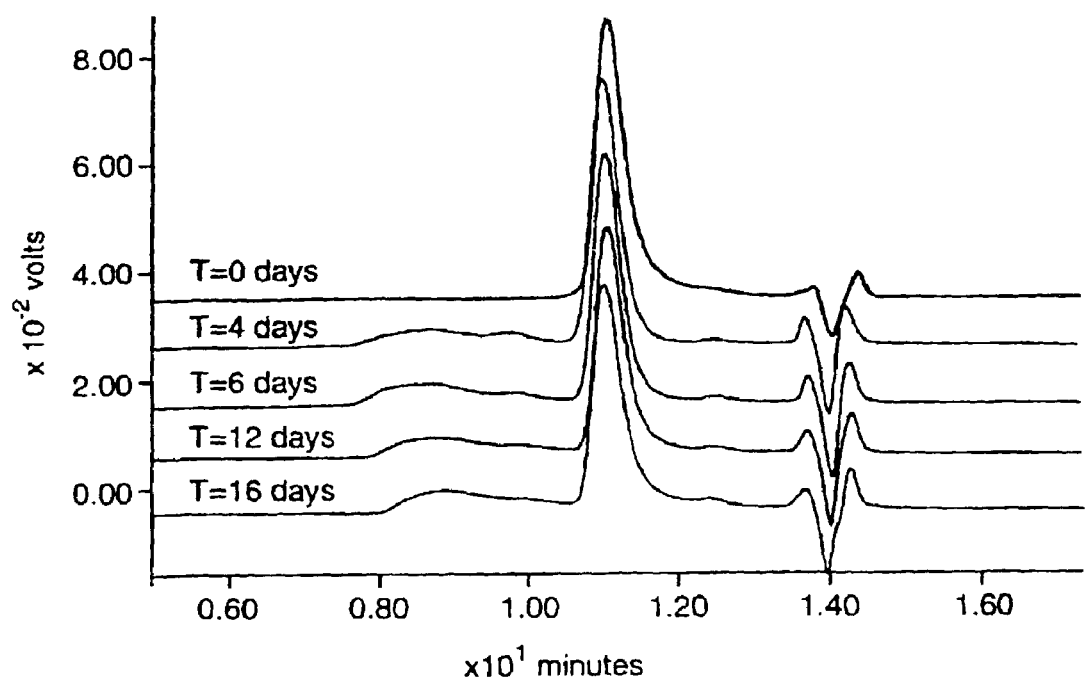
FIGS. 6A, 6B, and 6C are SEC-HPLC profiles for stability studies of N-terminally pegylated G-CSF or lysine 35 monopegylated G-CSF.
Figure 6B:
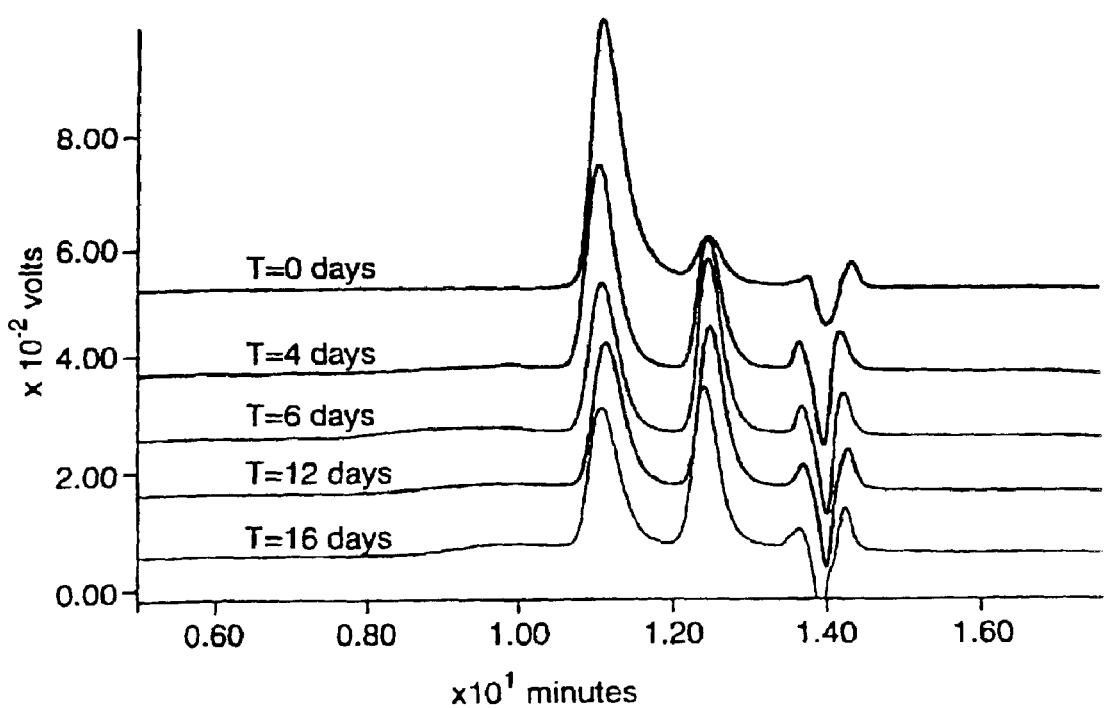
Figure 6C:
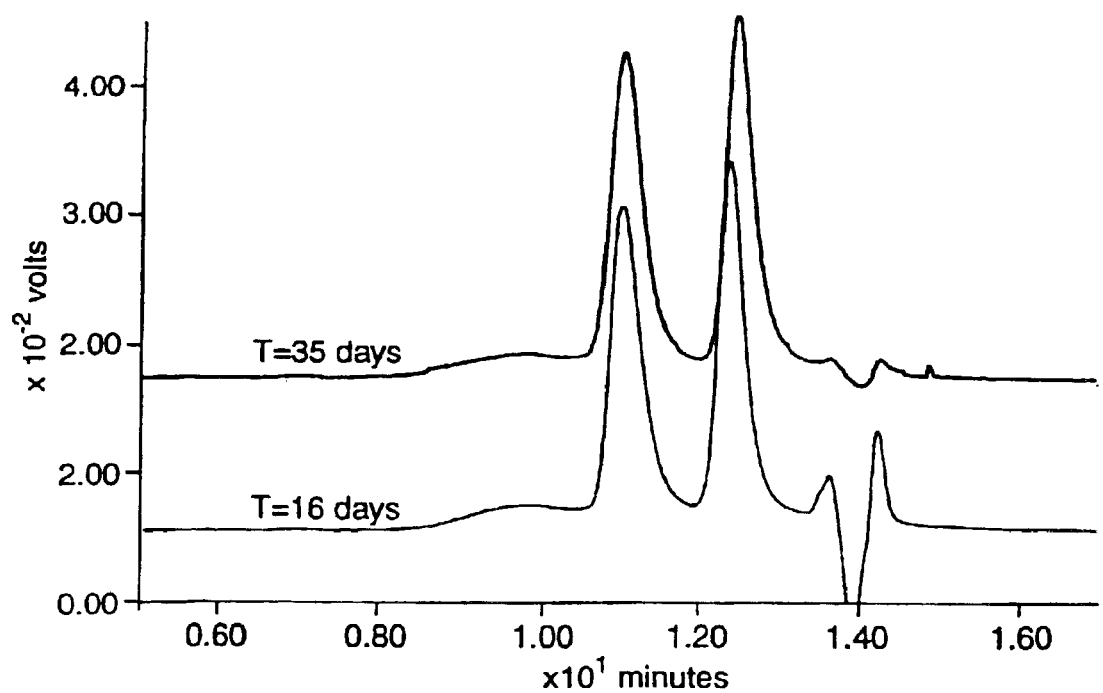

Stability was assessed in terms of breakdown of product, as visualized using SEC-HPLC. Methods: N-terminally pegylated G-CSF and lysine-35 monopegylated G-CSF were studied in two pH levels, pH 4.0 and pH 6.0 at 4° C., each for up to 16 days. Elevating the pH to 6.0 provides an environment for accelerated stability assays. For the pH 6.0 samples, N-terminal monopegylated G-CSF and Lysine 35 monopegylated G-CSF as prepared above were placed in a buffer containing 20 mM sodium phosphate, 5 mM sodium acetate, 2.5% mannitol, 0.005% Tween-80, pH 6.0 at a final protein concentration of 0.25 mg/ml. One ml aliquots were stored in 3 ml sterile injection vials. Vials of each was stored at 4° C. and 29° C. for up to 16 days. Stability was assessed by SEC-HPLC tracings. If the later measurements stayed the same (as ascertained by visual inspection) as the initial (Time=0) measurements, the sample was considered to be stable for that length of time. Results: Results are illustrated in FIGS. 6A-6C. (a) Comparison at pH 6.0 at 4° C. FIG. 6A shows the 4° C. SEC-HPLC profiles for N-terminally monopegylated G-CSF at pH 6 over time and FIG. 6B shows the 4° C. SEC-HPLC profiles for lysine-35 monopegylated G-CSF at pH 6 over time. One interpretation is that the Lys-35 material is breaking down to a material with a molecular weight similar to that of unmodified G-CSF. (b) Extended duration at pH 4.0 at 4° C. PH 4.0 and 4° C. provides something of a control illustrating relatively stable conditions in that the N-terminal species shows no degradation. For the Lys 35 species, the break down of the material is still occurring, but at a much slower rate. (c) Comparison at pH 6.0 at 4° C. FIG. 6C illustrates the SEC-HPLC profiles for the monopegylated G-CSF's under these conditions, under extended time periods. As can be seen, at pH 6.0 and 4° C., the lysine-35 material exhibits no increase in depegylation at day 16 or day 35 beyond what was seen for day 6 (FIG. 6B). This indicates that depegylation (instability) does not change, under those conditions, beyond day 6.

EXAMPLE 2

This example demonstrates a method of preparing a substantially homogenous population of monopegylated G-CSF using reductive alkylation, and characterization of this population. Recombinant G-CSF as described in the above example was used. As can be seen, not only do the present methods provide advantages in terms of yield of N-terminally chemically modified material, but also, the amine linkages of the present reductive alkylation process produce substantially more stable products as demonstrated by a large difference in the degree of aggregation upon storage.

A. Preparation of the Mono-methoxypolyethylene Glycol-GCSF Conjugates with the Site of Attachment at the N-Terminal α-Amino Residue.

To a cooled (4° C.), stirred solution of rhG-CSF (1 ml, 5 mg/ml as described in the Example above) in 100 mM sodium phosphate, pH 5, containing 20 mM $NaCNBH_3$, was added a 5-fold molar excess of methoxypolyethylene glycol aldehyde (MPEG)(average molecular weight, 6 kDa). The stirring of the reaction mixture was continued at the same temperature.

The extent of the protein modification during the course of the reaction was monitored by SEC HPLC using Bio-Sil SEC 250–5 column (BIO-RAD) eluted with 0.05 M $NaH_2PO_4$, 0.05 M $Na_2HPO_4$, 0.15 M NaCl, 0.01 M $NaN_3$, pH 6.8 at 1 ml/min.

Figure 7:
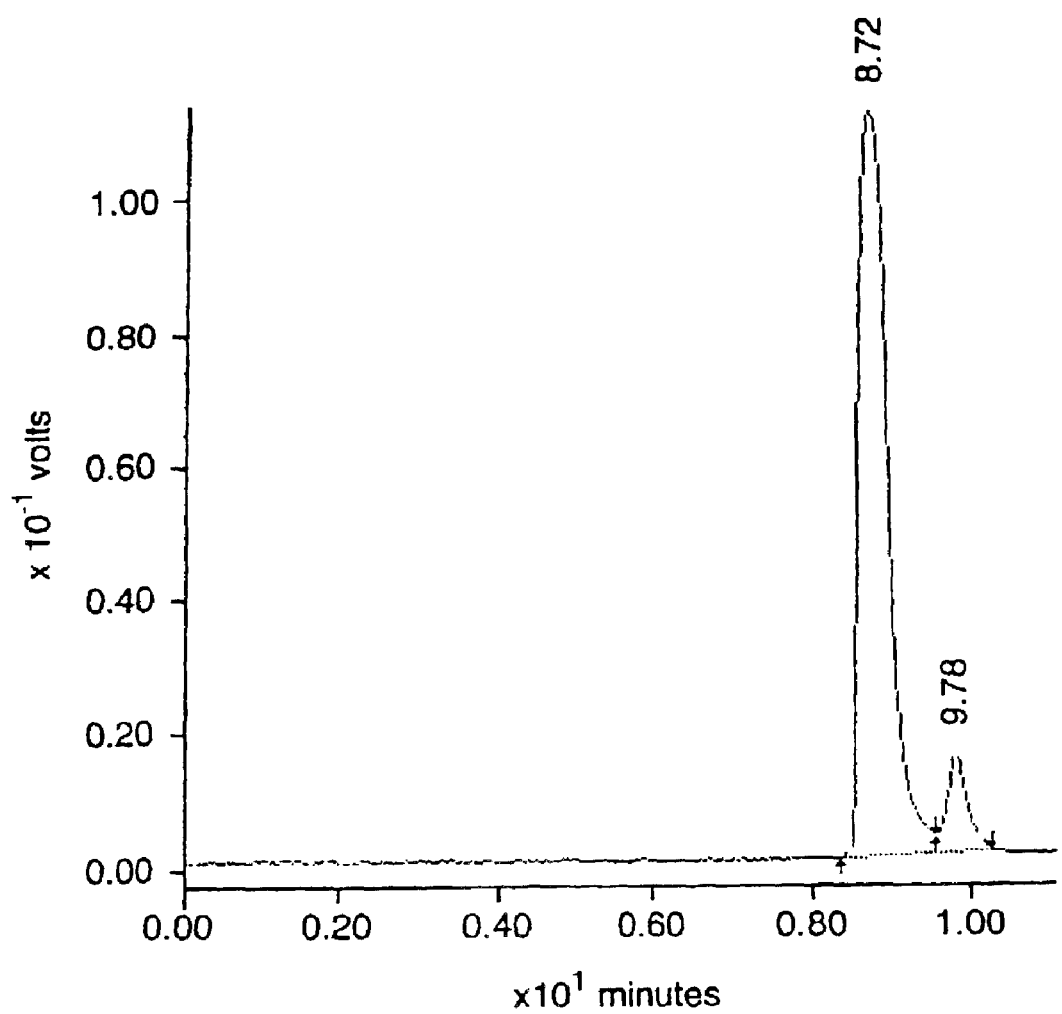
FIG. 7 illustrates size exclusion HPLC analysis of the reaction mixture in the process of reductive alkylation of rh-G-CSF with methoxypolyethylene glycol aldehyde (MW 6 kDa).

After 10 hours the SEC HPLC analysis indicated that 92% of the protein has been converted to the mono-MPEG-GCSF derivative. This can be seen in FIG. 7, which is a recording of the protein concentration (as determined by absorbance at $A_{280}$) and shows the peak eluting at 8.72 minutes as monopegylated G-CSF, and a minor peak of unreacted G-CSF eluting at 9.78 minutes.

Figure 8:
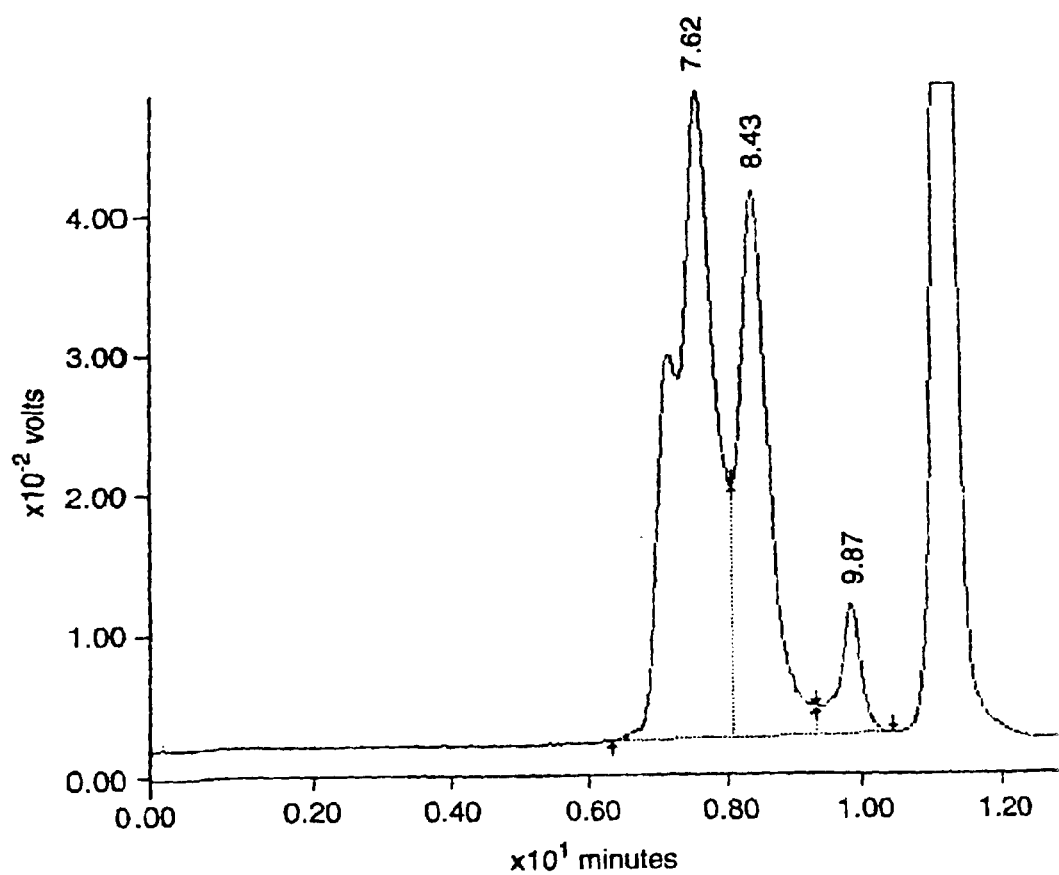
FIG. 8 illustrates size exclusion HPLC analysis of the reaction mixture using N-hydroxysuccinimidyl ester of MPEG, also at MW=6 kDa.

As a comparison, FIG. 8 shows the peaks obtained when using N-hydroxysuccinimidyl ester of MPEG. The molecular weight was also 6 kDa. As can be seen, the mixture obtained from this reaction was: tri-MPEG-GCSF conjugated (shoulder at approximately 7.25 minutes), di-MPEG-GCSF conjugate (peak at 7.62 minutes), mono-MPEG-GCSF conjugate (peak at 8.43 minutes) and unreacted G-CSF (peak at 9.87 minutes).

At this 10 hour time point, where 92% of the protein had been converted to monopegylated material, the pH of the reaction mixture was adjusted to pH 4 with 100 mM HCl and the reaction mixture was diluted 5 times with 1 mM HCl.

The mono-MPEG-GCSF derivative was purified by ion exchange chromatography using HiLoad 16/10 S Sepharose HP column (Pharmacia) equilibrated with 20 mM sodium acetate buffer, pH 4. The reaction mixture was loaded on the column at a flow rate of 1 ml/min and the unreacted MPEG aldehyde eluted with three column volumes of the same buffer. Then a linear 400 minute gradient from 0% to 45% 20 mM sodium acetate, pH 4, containing 1 M NaCl was used to the elute the protein-polymer conjugate at 4° C.

Fractions containing the mono-MPEG-GCSF derivative were pooled, concentrated and sterile filtered.

Various mono-MPEG-GCSF conjugates obtained by modifying rh-G-CSF with MPEG aldehydes of different average molecular weight (12, 20 and 25 kDa) were prepared in a similar manner.

B. Analysis of Monopegylated G-CSF
1. Molecular Weight

The molecular weight at the monopegylated conjugates was determined by SDS-PAGE, gel filtration, matrix assisted laser desorption mass spectrometry, and equilibrium centrifugation. These results are presented in Table 4, below.

TABLE 4

Molecular Weights of N-terminally Alkylated Mono-MPEG-GCSF Conjugates

| Conjugate | MW estimated | MW gel filtration | MW mass spectometry | MW ultra-centrifugation |
| --- | --- | --- | --- | --- |
| MPEG-(6kDa)-GCSF | 24800 | 53024 | 24737 | 25548 |
| MPEG-(12kDa)-GCSF | 30800 | 124343 | 30703 | 29711 |
| MPEG-(20kDa)-GCSF | 38800 | 221876 | 38577 | 38196 |
| MPEG-(25kDa)-GCSF | 43800 | 333266 | N/D | N/D |

The structure of the prepared N-terminal mono-MPEG-GCSF conjugates was confirmed using the methods of N-terminal protein sequencing and peptide mapping. Cyanogen bromide cleavage of the N-terminal methionyl residue resulted in removal of the polyethylene glycol.

2. Biological Activity

The in vitro biological activity of the pegylated MPEG-GCSF conjugates was determined by measuring the stimulated uptake of $^3$H thymidine into mouse bone marrow cells.

The in vivo biological activity was determined by subcutaneous injection to hamsters MPEG-GCSF conjugates or rhG-CSF (at 100 mg/kg) and measuring total white blood cell count. Bioactivity as compared to non-derivatized G-CSF was calculated as the area under the WBC/time curve after subtracting the vehicle control curve. Relative bioactivity of the MPEG-GCSF derivatives was expressed as the percentage bioactivity compared to unmodified G-CSF.

Figure 9:
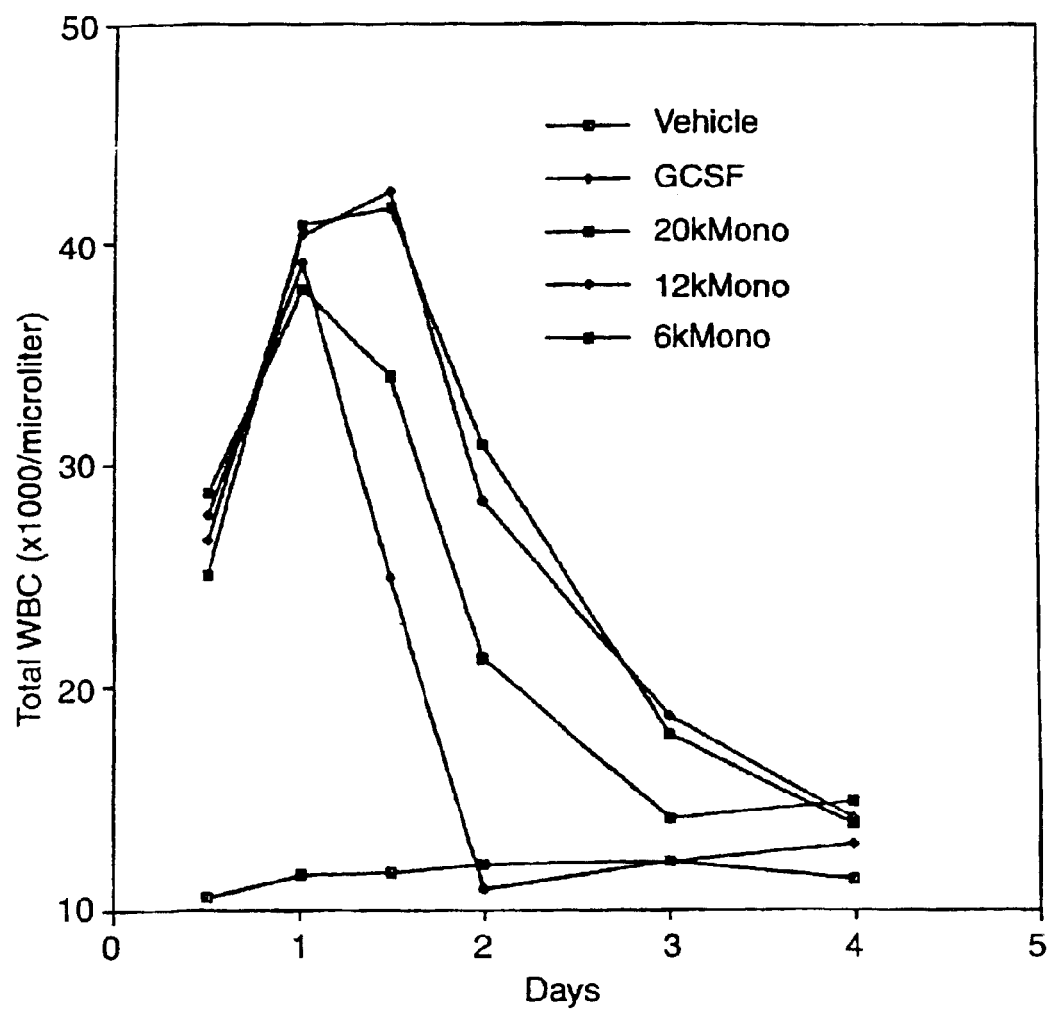
FIG. 9 illustrates the total white blood cell response after a single subcutaneous dose to mono-N terminal MPEG-GCSF conjugates prepared by reductive alkylation of rh-G-CSF with MPEG aldehydes of different molecular weights (6 kDa, 12 kDa and 20 kDa).

This is illustrated in FIG. 9, which is a graph illustrating the total white blood cell response to mono-N-terminal MPEG-GCSF conjugates prepared by reductive alkylation of rhG-CF with MPEG aldehydes of different molecular weights (6 kDa, 12 kDa, and 20 kDa). As can be seen, all monopegylated molecules elicited a response. The higher the molecular weight of the polyethylene glycol moiety used, the higher the white blood cell count achieved, except the 12 kDa achieved a slightly higher count than did the 20 kDa version at day 2.

3. Stability Studies

N-terminally pegylated G-CSF's prepared by the two different chemistries (amide vs. amine of the reductive alkylation here) were compared for the degree of aggregation. Unexpectedly, N-terminally pegylated G-CSF using the amine chemistry was found to be substantially more stable than N-terminally pegylated G-CSF with an amide linkage (NHS chemistry as described in Example 1).

Methods: Both N-terminally pegylated G-CSF samples were in 10 mM NaOac pH4.0 with 5% sorbitol, at a concentration of 1 mg protein/ml. The G-CSF's were pegylated with PEG 6000 for each. The amide-linked conjugate was prepared as in Example 1, and the amine linked conjugate was prepared as in Example 2. Six samples of each were stored for eight weeks at 45° C. At the end of eight weeks, the degree of aggregation was determined using size exclusion chromatography and ion exchange chromatography.

Results: The results demonstrate that the present reductive alkylation method is advantageous over aceylation because, surprisingly, it produces a material with far fewer aggregates after 8 weeks at elevated temperatures. The table below shows the percent of non-aggregated material ("main peak" material) for both materials using size exclusion chromatography (SEC) or ion exchange (IE):

TABLE 5

| Sample: 8 wks, 45° C. | % Main Peak SEC/IE |
| --- | --- |
| Amine | 82%/84% |
| Amide | 37%/65%* |

*This is relatively high because ion exchange does not allow for full analysis of the aggregation.

EXAMPLE 3

This example demonstrates chemically modified consensus interferon. More specifically, this example demonstrates a method of preparing a substantially homogenous population of monopegylated IFN-con$_1$, and characterization of this population.

It should be noted that while the present example uses IFN-con$_1$, any of the consensus interferons as set forth above may be chemically modified. Such chemical modification may be with any of the water soluble polymers as listed above, although PEG is used here. For pegylation, PEG 12000 is used here, although any water soluble PEG species may be used (PEG 12000 was selected for ease in handling and convenience). Again, a variety of means for chemical modification are available (such as acetylation) but, for selective N-terminal chemical modification, such as N-terminal pegylation, the present reductive alkylation method as described in this example is preferred.

A. Preparation of Consensus Interferon

Figure 2:
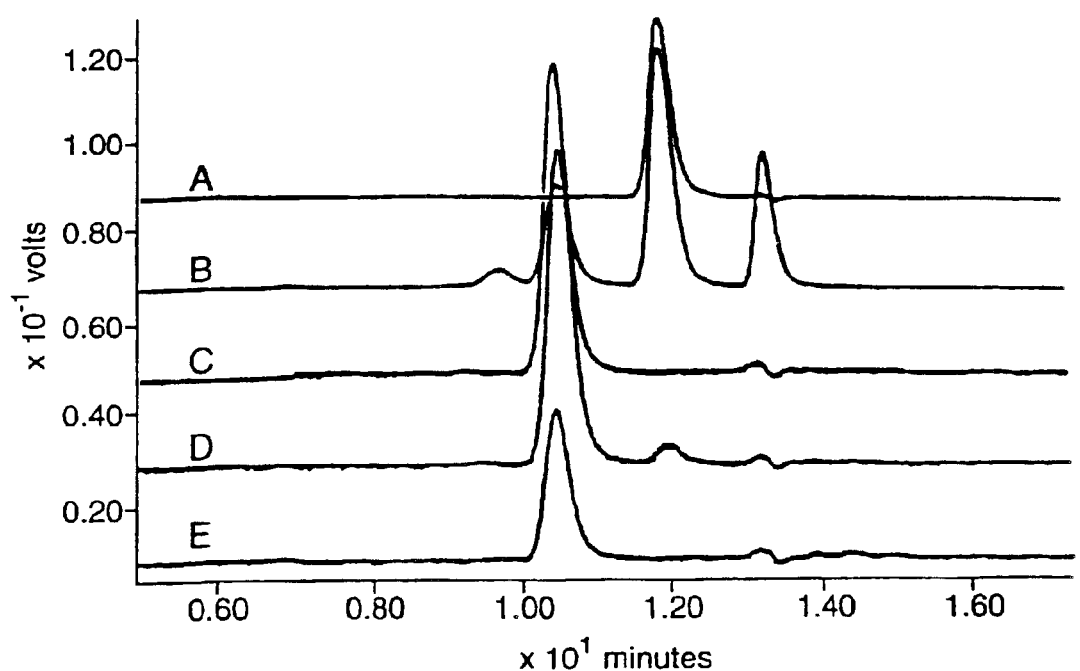
FIG. 2 is an SEC-HPLC profile of (Line A) recombinant human methionyl G-CSF standard; (Line B) SCM-PEG-GCSF reaction mix; (Line C) N-terminally pegylated G-CSF; (Line D) lysine 35 monopegylated G-CSF; (Line E) lysine 41 monopegylated G-CSF.

IFN-αcon$_1$ (here referred to as IFN-con$_1$) as described in FIG. 2 of U.S. Pat. No. 4,695,623, which is incorporated by reference in its entirety, was used for the preparation of monopegylated consensus interferon. The IFN-con$_1$ was produced by expression of exogenous DNA in bacteria, and contained a methionyl residue at the N-terminus.

B. Pegylation of Consensus Interferon

To a cooled (4° C.), stirred solution of IFN-con$_1$ (3.45 mg/ml, containing 35.25% of the N-terminally blocked form) in 100 mM sodium phosphate, pH 4.0, containing 20 mM NaCNBH$_3$ was added a 8-fold molar excess of methoxypolyethylene glycol aldehyde (MPEG)(average molecular weight 12 kDa).

The extent of the protein modification during the course of the reaction was monitored by reverse phase HPLC using a polymer-based poly(styrene/divinylbenzene) column, such as PLRP-S (PL Separation Sciences Polymer Laboratories).

After 10 hours the reverse phase HPLC analysis indicated that 80% of the protein with unblocked α-amino group at the N-terminus has been converted to the MPEG-IFN-con$_1$ derivative.

At the 10 hour time point, the reaction mixture was diluted 5 times with water and the mono-MPEG-IFN-Con$_1$ derivative was purified by ion exchange chromatography using HiLoad 16/10 S Sepharose HP column (Pharmacia) equilibrated with 20 mM sodium acetate buffer, pH 4.0. The reaction mixture was loaded on the column at a flow rate of 1 ml/min and the unreacted MPEG aldehyde eluted with three column volumes of the same buffer. Then a linear 420 minute gradient from 0% to 75% of 20 mM sodium acetate, pH 4.0, containing 1 M NaCl was used to the elute the protein-polymer conjugate at 4° C.

Fractions containing the mono-MPEG-IFN-Con$_1$ derivative were pooled, concentrated and sterile filtered.

C. Analysis of Monopegylated Consensus Interferon

1. Homogeneity

The homogeneity of the purified mono-MPEG-IFN-Con$_1$ conjugates was determined by SDS-PAGE using 10–20% or 4–20% precast gradient gels (Integrated Separation Systems). The gels showed a main band at MW 35 kDa.

To characterize the effective size (hydrodynamic radius) of each mono-MPEG-IFN-con$_1$ species a Superose 6 HR 10/30 (Pharmacia) gel filtration column was used. Proteins were detected by UV absorbance at 280 nm. The BIO-RAD gel filtration standards served as globular protein molecular weight markers.

The structure of the purified N-terminal mono-MPEG-IFN-con$_1$ conjugates was confirmed using the methods of N-terminal protein sequencing and peptide mapping.

It is noted that this IFN-con$_1$ preparation contained some N-terminally blocked material, and this material was not pegylated. The material which was pegylated, however, was monopegylated at the N-terminus. Thus, in this type of situation, one may wish to use other means to separate the blocked from the unblocked material, such as ion exchange or size exclusion chromatography.

2. Biological Activity

The in vitro biological activity of the mono-MPEG-IFN Con$_1$ conjugates was determined by measuring their antiviral bioactivity. The in vitro biological activity of the mono-MPEG-IFN-Con$_1$ conjugates was determined by measuring their antiviral bioactivity in human (HeLa) cells.

It was found that the mono-MPEG (12 kDa)-IFN-Con$_1$ conjugate shows 20% in vitro bioactivity (in U/mg of protein) when compared to the unmodified species. As noted above for pegylated G-CSF, the in vitro assays, while useful to demonstrate biological activity, may show a rather low level of activity for chemically modified proteins because of characteristic sustained release. The in vivo biological activity may be higher than the in vitro biological activity.

D. Chemically Modified Consensus Interferon with the N-Terminally Blocked Molecules Removed The present reductive alkylation was also performed on the above IFN-con$_1$ which had the portion of N-terminally blocked molecules pre-removed. Both PEG 12000 and PEG 20000 were used in the reductive alkylation method as described above.

The molecular apparent molecular weights were as follow:

| Conjugate | Apparent MW by Gel Filtration | Apparent MW by SDS-PAGE |
| --- | --- | --- |
| monoMPEG (12kDa) IFN-con$_1$ | 104.0 kDa | 35.6 kDa |
| monoMPEG (20kDa) IFN-con$_1$ | 175.1 kDa | 55.4 kDa |

Analysis of the IFN-con$_1$ 20 kDa PEG conjugate using FPLC ion exchange chromatography resulted in three peaks:

MonoMPEG-IFN-con$_1$: 66% of the total area (eluting at 265.93 ml)

Protein aggregate and oligo MPEG-IFN-con$_1$ conjugate: 24% of the total area (eluting at 238.42 ml); and Unreacted IFN-con$_1$: 10% of the total area (eluting at 328.77 ml).

The conditions were not further optimized. One may further separate the monopegylated material using chromatographic or other methods.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. An antiviral, pegylated consensus interferon.

2. The antiviral, pegylated consensus interferon of claim 1 that is an anti-hepatitis viral, pegylated consensus interferon.

3. The antiviral, pegylated consensus interferon of claim 1 that is an antihepatitis C viral, pegylated consensus interferon.

4. The anti-hepatitis C viral, pegylated consensus interferon of claim 3 wherein said consensus interferon is selected from from the group consisting of IFN-con$_1$, IFN-con$_2$, and IFN-con$_3$.

5. The anti-hepatitis C viral, pegylated consensus interferon of claim 4 wherein said consensus interferon is IFN-con$_1$.

6. The anti-hepatitis C viral, pegylated consensus interferon of claim 4 wherein said consensus interferon is IFN-con$_2$.

7. The anti-hepatitis C viral, pegylated consensus interferon of claim 4 wherein said consensus interferon is IFN-con$_3$.

8. The antiviral, pegylated consensus interferon of claim 1 that is an antiviral, monopegylated consensus interferon.

9. N-terminally pegylated consensus interferon.

10. N-terminally pegylated consensus interferon of claim 9 wherein said consensus interferon is selected from the group consisting of IFN-con$_1$, IFN-con$_2$, and IFN-con$_3$.

11. N-terminally pegylated consensus interferon of claim 10 wherein said consensus interferon is IFN-con$_1$.

12. N-terminally pegylated consensus interferon of claim 10 wherein said consensus interferon is IFN-con$_2$.

13. N-terminally pegylated consensus interferon of claim 10 wherein said consensus interferon is IFN-con$_3$.

14. N-terminally monopegylated consensus interferon.

15. A pharmaceutical composition comprising:
  (a) antiviral, pegylated consensus interferon; and
  (b) a pharmaceutically acceptable diluent, adjuvant or carrier.

16. The pharmaceutical composition of claim 15 that is essentially free of consensus interferon PEGylated at sites other than the N-terminus.

17. The pharmaceutical composition of claim 15 werein said consensus interferon is selected from the group consisting of IFN-con$_1$, IFN-con$_2$, and IFN-con$_3$.

18. The pharmaceutical composition of claim 17 wherein said consensus interferon is IFN-con$_1$.

19. The pharmaceutical composition of claim 17 wherein said consensus interferon is IFN-con$_2$.

20. The pharmaceutical composition of claim 17 wherein said consensus interferon is IFN-con$_3$.

21. The pharmaceutical composition of claim 15 wherein said consensus interferon is monopegylated.

22. A pharmaceutical composition comprising:
  (a) N-terminally pegylated consensus interferon; and
  (b) a pharmaceutically acceptable diluent, adjuvant or carrier.

23. The pharmaceutical composition of claim 22 that is essentially free of consensus interferon PEGylated at sites other than the N-terminus.

24. The pharmaceutical composition of claim 22 wherein said consensus interferon is selected from the group consisting of IFN-con$_1$, IFN-con$_2$, and IFN-con$_3$.

25. The pharmaceutical composition of claim 24 wherein said consensus interferon is IFN-con$_1$.

26. The pharmaceutical composition of claim 24 wherein said consensus interferon is IFN-con$_2$.

27. The pharmaceutical composition of claim 24 wherein said consensus interferon is IFN-con$_3$.

28. The pharmaceutical composition of claim 25 wherein said consensus interferon is monopegylated.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 531 base pairs
      (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO: 1:

ATGACTCCAT TAGGTCCTGC TTCTTCTCTG CCGCAAAGCT TTCTGCTGAA ATGTCTGGAA      60

CAGGTTCGTA AAATCCAGGG TGACGGTGCT GCACTGCAAG AAAAACTGTG CGCTACTTAC     120

AAACTGTGCC ATCCGGAAGA GCTGGTACTG CTGGGTCATT CTCTTGGGAT CCCGTGGGCT     180

CCGCTGTCTT CTTGTCCATC TCAAGCTCTT CAGCTGGCTG GTTGTCTGTC TCAACTGCAT     240

TCTGGTCTGT TCCTGTATCA GGGTCTTCTG CAAGCTCTGG AAGGTATCTC TCCGGAACTG     300

GGTCCGACTC TGGACACTCT GCAGCTAGAT GTAGCTGACT TGCTACTAC TATTTGGCAA      360

CAGATGGAAG AGCTCGGTAT GGCACCAGCT CTGCAACCGA CTCAAGGTGC TATGCCGGCA     420

TTCGCTTCTG CATTCCAGCG TCGTGCAGGA GGTGTACTGG TTGCTTCTCA TCTGCAATCT     480

TTCCTGGAAG TATCTTACCG TGTTCTGCGT CATCTGGCTC AGCCGTAATA G             531

(2) INFORMATION FOR SEQ ID NO: 2:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Met Thr Pro Leu Gly Pro Ala Ser Ser Leu Pro Gln Ser Phe Leu Leu
1               5                  10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110 he Ala Thr Thr Ile Trp Gln Gln Met Glu Glu Leu Gly Met Ala
    115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```